US009215895B2

(12) United States Patent
Bowen et al.

(10) Patent No.: US 9,215,895 B2
(45) Date of Patent: Dec. 22, 2015

(54) NICOTINE SALT FORMULATIONS FOR AEROSOL DEVICES AND METHODS THEREOF

(71) Applicant: PAX Labs, Inc., San Francisco, CA (US)

(72) Inventors: Adam Bowen, San Francisco, CA (US); Chenyue Xing, San Francisco, CA (US)

(73) Assignee: PAX Labs, Inc., San Francisco, CA (US)

( * ) Notice: Subject to any disclaimer, the term of this patent is extended or adjusted under 35 U.S.C. 154(b) by 0 days.

(21) Appl. No.: 14/512,311

(22) Filed: Oct. 10, 2014

(65) Prior Publication Data

US 2015/0020824 A1    Jan. 22, 2015

Related U.S. Application Data

(63) Continuation of application No. 14/271,071, filed on May 6, 2014.

(60) Provisional application No. 61/912,507, filed on Dec. 5, 2013, provisional application No. 61/820,128, filed on May 6, 2013.

(51) Int. Cl.
*A24F 47/00* (2006.01)
*A24B 15/16* (2006.01)
*A61K 31/465* (2006.01)
*A61K 9/12* (2006.01)

(52) U.S. Cl.
CPC .............. *A24F 47/008* (2013.01); *A24B 15/16* (2013.01); *A61K 9/12* (2013.01); *A61K 31/465* (2013.01)

(58) Field of Classification Search
CPC .................................................. A24F 47/008
See application file for complete search history.

(56) References Cited

U.S. PATENT DOCUMENTS

| | | |
|---|---|---|
| 374,584 A | 12/1887 | Cook |
| 576,653 A | 2/1897 | Bowlby |
| 595,070 A | 12/1897 | Oldenbusch |
| 799,844 A | 9/1905 | Fuller |
| 969,076 A | 8/1910 | Pender |
| 1,067,531 A | 7/1913 | MacGregor |
| 1,163,183 A | 12/1915 | Stoll |
| 1,299,162 A | 4/1919 | Fisher |
| 1,505,748 A | 3/1924 | Tamis |
| 1,552,877 A | 9/1925 | Phillipps et al. |
| 1,632,335 A | 6/1927 | Hiering |
| 1,706,244 A | 3/1929 | Meyerson |
| 1,845,340 A | 2/1932 | Ritz |
| 1,972,118 A | 9/1934 | McDill |
| 1,998,683 A | 4/1935 | Montgomery |
| 2,031,363 A | 2/1936 | Erikson |
| 2,039,559 A | 5/1936 | Segal |
| 2,327,120 A | 11/1940 | McCoon |
| 2,231,909 A | 2/1941 | Hempel |
| 2,460,427 A | 2/1949 | Musselman et al. |
| 2,483,304 A | 9/1949 | Vogel |
| 2,502,561 A | 4/1950 | Ebert |
| 2,765,949 A | 10/1956 | Hillman |
| 2,897,958 A | 8/1959 | Tarleton |
| 3,146,937 A | 9/1964 | Vesak |
| 3,420,360 A | 1/1969 | Young |
| 3,567,014 A | 3/1971 | Feigelman |
| 3,861,523 A | 1/1975 | Fountain et al. |
| 3,941,300 A | 3/1976 | Troth |
| 4,207,976 A | 6/1980 | Herman |
| 4,519,319 A | 5/1985 | Howlett |
| 4,771,796 A | 9/1988 | Myer |
| 4,798,310 A | 1/1989 | Kasai et al. |
| 4,813,536 A | 3/1989 | Willis |
| 4,830,028 A | 5/1989 | Lawson et al. |
| 4,836,224 A | 6/1989 | Lawson et al. |
| 4,848,563 A | 7/1989 | Robbins |
| 5,005,759 A | 4/1991 | Bouche |
| 5,123,530 A | 6/1992 | Lee |
| 5,269,327 A | 12/1993 | Counts et al. |
| 5,605,226 A | 2/1997 | Hernlein |
| 5,641,064 A | 6/1997 | Goserud |
| 5,746,587 A | 5/1998 | Racine et al. |
| 5,810,164 A | 9/1998 | Rennecamp |
| 5,881,884 A | 3/1999 | Podosek |
| 5,938,018 A | 8/1999 | Keaveney et al. |
| 5,967,310 A | 10/1999 | Hill |
| 5,975,415 A | 11/1999 | Zehnal |
| 5,979,460 A | 11/1999 | Matsumura |
| 6,102,036 A | 8/2000 | Slutsky et al. |
| 6,234,169 B1 | 5/2001 | Bulbrook et al. |
| 6,269,966 B1 | 8/2001 | Pallo et al. |

(Continued)

FOREIGN PATENT DOCUMENTS

| | | |
|---|---|---|
| CN | 101869356 A | 10/2010 |
| CN | 102754924 A | 10/2012 |
| EP | 0354661 A2 | 2/1990 |
| EP | 1618803 | 1/2006 |
| EP | 2186507 | 5/2010 |
| EP | 2325093 | 5/2011 |
| EP | 2609821 A1 | 7/2013 |
| JP | 02145179 | 11/2000 |
| JP | 2001-165437 A | 6/2001 |
| JP | 09075058 | 9/2007 |
| WO | WO97/12639 | 4/1997 |
| WO | WO 03/094900 | 11/2003 |
| WO | WO 2011/033396 | 3/2011 |
| WO | WO 2011/117580 A2 | 9/2011 |
| WO | WO 2011/139684 | 11/2011 |
| WO | WO 2012/021972 | 2/2012 |

(Continued)

OTHER PUBLICATIONS

International search report and written opinion dated Sep. 5, 2014 for PCT Application No. US2014/037019.

(Continued)

*Primary Examiner* — Richard Crispino
*Assistant Examiner* — Dionne Walls Mayes
(74) *Attorney, Agent, or Firm* — Shay Glenn LLP

(57) ABSTRACT

A nicotine salt liquid formulation for generating an inhalable aerosol in an electronic cigarette comprising nicotine salt that forms about 0.5% to about 20% nicotine is provided.

26 Claims, 8 Drawing Sheets

(56) References Cited

U.S. PATENT DOCUMENTS

| | | |
|---|---|---|
| 6,386,371 B1 | 5/2002 | Parsons |
| 6,431,363 B1 | 8/2002 | Hacker |
| 6,446,793 B1 | 9/2002 | Layshock |
| 6,510,982 B2 | 1/2003 | White et al. |
| 6,557,708 B2 | 5/2003 | Polacco |
| 6,622,867 B2 | 9/2003 | Menceles |
| 6,672,762 B1 | 1/2004 | Faircloth |
| 6,726,006 B1 | 4/2004 | Funderburk et al. |
| 6,799,576 B2 | 10/2004 | Farr |
| 6,874,507 B2 | 4/2005 | Farr |
| 7,000,775 B2 | 2/2006 | Gelardi |
| D557,209 S | 12/2007 | Ahlgren et al. |
| 7,374,048 B2 | 5/2008 | Mazurek |
| 7,546,703 B2 | 6/2009 | Johnske et al. |
| 7,621,403 B2 | 11/2009 | Althoff et al. |
| 7,644,823 B2 | 1/2010 | Gelardi et al. |
| D611,409 S | 3/2010 | Green et al. |
| 7,767,698 B2 | 8/2010 | Warchol et al. |
| 7,815,332 B1 | 10/2010 | Smith |
| 7,832,410 B2 | 11/2010 | Hon |
| 7,886,507 B2 | 2/2011 | McGuinness, Jr. |
| 7,988,034 B2 | 8/2011 | Pezzoli |
| D649,932 S | 12/2011 | Symons |
| 8,079,371 B2 | 12/2011 | Robinson et al. |
| 8,141,701 B2 | 3/2012 | Hodges |
| 8,156,944 B2 | 4/2012 | Han |
| 8,322,350 B2 | 12/2012 | Lipowicz |
| D674,748 S | 1/2013 | Ferber et al. |
| 8,375,957 B2 | 2/2013 | Hon |
| 8,381,739 B2 * | 2/2013 | Gonda ............ 131/270 |
| 8,443,534 B2 | 5/2013 | Goodfellow et al. |
| 8,464,867 B2 | 6/2013 | Holloway et al. |
| D686,987 S | 7/2013 | Vanstone et al. |
| 8,511,318 B2 | 8/2013 | Hon |
| 8,539,959 B1 | 9/2013 | Scatterday |
| 8,596,460 B2 | 12/2013 | Scatterday |
| D700,572 S | 3/2014 | Esses |
| D704,629 S | 5/2014 | Liu |
| D704,634 S | 5/2014 | Eidelman et al. |
| 8,741,348 B2 | 6/2014 | Hansson et al. |
| 2001/0032795 A1 | 10/2001 | Weinstein et al. |
| 2001/0052480 A1 | 12/2001 | Kawaguchi et al. |
| 2002/0043554 A1 | 4/2002 | White et al. |
| 2002/0175164 A1 | 11/2002 | Dees et al. |
| 2003/0089377 A1 | 5/2003 | Hajaligol et al. |
| 2004/0099266 A1 | 5/2004 | Cross et al. |
| 2004/0149624 A1 | 8/2004 | Wischusen, III et al. |
| 2004/0191322 A1 | 9/2004 | Hansson |
| 2005/0061759 A1 | 3/2005 | Doucette |
| 2005/0118545 A1 | 6/2005 | Wong |
| 2005/0145533 A1 | 7/2005 | Seligson |
| 2005/0172976 A1 | 8/2005 | Newman et al. |
| 2006/0018840 A1 | 1/2006 | Lechuga-Ballesteros et al. |
| 2006/0054676 A1 | 3/2006 | Wischusen, III |
| 2006/0150991 A1 | 7/2006 | Lee |
| 2006/0196518 A1 * | 9/2006 | Hon ............ 131/360 |
| 2006/0254948 A1 | 11/2006 | Herbert et al. |
| 2006/0255105 A1 | 11/2006 | Sweet |
| 2007/0062548 A1 | 3/2007 | Horstmann et al. |
| 2007/0074734 A1 | 4/2007 | Braunshteyn et al. |
| 2007/0098148 A1 | 5/2007 | Sherman |
| 2007/0144514 A1 | 6/2007 | Yeates et al. |
| 2007/0163610 A1 | 7/2007 | Lindell et al. |
| 2007/0235046 A1 | 10/2007 | Gedevanishvili |
| 2007/0267033 A1 | 11/2007 | Mishra et al. |
| 2008/0029095 A1 | 2/2008 | Esser |
| 2008/0092912 A1 | 4/2008 | Robinson et al. |
| 2008/0241255 A1 | 10/2008 | Rose et al. |
| 2008/0276947 A1 | 11/2008 | Martzel |
| 2009/0004249 A1 | 1/2009 | Gonda |
| 2009/0095311 A1 | 4/2009 | Han |
| 2009/0151717 A1 * | 6/2009 | Bowen et al. ............ 128/200.23 |
| 2009/0267252 A1 | 10/2009 | Ikeyama |
| 2009/0288669 A1 | 11/2009 | Hutchens |
| 2009/0293895 A1 | 12/2009 | Axelsson |
| 2010/0000672 A1 | 1/2010 | Fogle |
| 2010/0031968 A1 | 2/2010 | Sheikh et al. |
| 2010/0186757 A1 | 7/2010 | Crooks et al. |
| 2010/0200006 A1 | 8/2010 | Robinson et al. |
| 2010/0242974 A1 | 9/2010 | Pan |
| 2010/0242976 A1 | 9/2010 | Katayama et al. |
| 2010/0275938 A1 | 11/2010 | Roth et al. |
| 2010/0276333 A1 | 11/2010 | Couture |
| 2010/0307116 A1 | 12/2010 | Fisher |
| 2011/0049226 A1 | 3/2011 | Moreau et al. |
| 2011/0155153 A1 | 6/2011 | Thorens et al. |
| 2011/0162667 A1 | 7/2011 | Burke et al. |
| 2011/0168194 A1 | 7/2011 | Hon |
| 2011/0180433 A1 | 7/2011 | Rennecamp |
| 2011/0192397 A1 | 8/2011 | Saskar et al. |
| 2011/0232654 A1 | 9/2011 | Mass |
| 2011/0265806 A1 | 11/2011 | Alarcon et al. |
| 2011/0268809 A1 | 11/2011 | Brinkley et al. |
| 2011/0277780 A1 | 11/2011 | Terry et al. |
| 2011/0278189 A1 | 11/2011 | Terry et al. |
| 2011/0315701 A1 | 12/2011 | Everson |
| 2012/0006342 A1 | 1/2012 | Rose et al. |
| 2012/0060853 A1 | 3/2012 | Robinson et al. |
| 2012/0111347 A1 | 5/2012 | Hon |
| 2012/0199146 A1 | 8/2012 | Marangos |
| 2012/0204889 A1 | 8/2012 | Xiu |
| 2012/0227753 A1 | 9/2012 | Newton |
| 2012/0261286 A1 | 10/2012 | Holloway et al. |
| 2012/0267383 A1 | 10/2012 | Van Rooyen |
| 2012/0255567 A1 | 2/2013 | Gonda |
| 2013/0042865 A1 | 2/2013 | Monsees et al. |
| 2013/0140200 A1 | 6/2013 | Scatterday |
| 2013/0186416 A1 | 7/2013 | Gao |
| 2013/0228191 A1 | 9/2013 | Newton |
| 2013/0247924 A1 | 9/2013 | Scatterday et al. |
| 2013/0248385 A1 | 9/2013 | Scatterday et al. |
| 2013/0255702 A1 | 10/2013 | Griffith, Jr. et al. |
| 2013/0276802 A1 | 10/2013 | Scatterday |
| 2013/0284190 A1 | 10/2013 | Scatterday et al. |
| 2013/0284191 A1 | 10/2013 | Scatterday et al. |
| 2013/0333700 A1 | 12/2013 | Buchberger |
| 2014/0014124 A1 | 1/2014 | Glasberg et al. |
| 2014/0196731 A1 | 7/2014 | Scatterday |
| 2014/0261474 A1 * | 9/2014 | Gonda ............ 131/270 |
| 2014/0345631 A1 | 11/2014 | Bowen |
| 2014/0345635 A1 | 11/2014 | Rabinowitz et al. |

FOREIGN PATENT DOCUMENTS

| | | |
|---|---|---|
| WO | WO-2013083635 A1 | 6/2013 |
| WO | WO 2013/141906 | 9/2013 |
| WO | WO 2013/141907 | 9/2013 |
| WO | WO 2013/141994 | 9/2013 |
| WO | WO 2013/141998 | 9/2013 |
| WO | WO 2013/142671 | 9/2013 |
| WO | WO 2013/142678 | 9/2013 |
| WO | WO-2014093127 A2 | 6/2014 |
| WO | WO 2014/113592 | 7/2014 |
| WO | WO 2014/182736 | 11/2014 |
| WO | WO 2014/190079 | 11/2014 |
| WO | WO-2015100361 A1 | 7/2015 |

OTHER PUBLICATIONS

Summary of evaluations performed by the Joint FAO/WHO expert committee on food additives. (Mar. 10, 2003) http://www.inchem.org/documents/jecfa/jeceval/jec_1266.htm.

Summary of evaluations performed by the Joint FAO/WHO expert committee on food additives. (May 28, 2005) http://www.inchem.org/documents/jecfa/jeceval/jec_184.htm.

Inspections, compliance, enforcement and criminal investigations compliance actions and activities warning letters 2002. The compounding pharmacy (Apr. 9, 2002) htttb://www.fda.gov/ICECI/EnforcementActions/WarningLetters/2002/ucm144843.htm.

Summary of evaluations performed by the Joint FAO/WHO expert committee on food additives. (Jan. 29, 2003) http://www.inchem.org/documents/jecfa/jeceval/jec_2072.htm.

(56) References Cited

OTHER PUBLICATIONS

Summary of evaluations performed by the Joint FAO/WHO expert committee on food additive. (May 29, 2005) http://www.inchem.org/documents/jecfa/jeceval/jec_2181.htm.

Flouris, et al., Acute impact of active and passive electronic cigarette smoking on serum cotinine and lung function. Toxicol. 25(2):91-101 (2013).

Goniewicz, et al., Nicotine levels in electronic cigarettes. Nicotine Tob Res. 15(1):158-66 (2013).

Ingebrethsen, et al., Electronic cigarette aerosol particle size distribution measurements. Inhal Toxicol. 24(14):976-84 (2012).

Seeman, et al., The form of nicotine in tobacco. Thermal transfer of nicotine and nicotine acid salts to nicotine in the gas phase. J Agric Food Chem. 47(12):5133-45 (1999).

Vansickel, et al., A clinical laboratory model for evaluating the acute effects of electronic "cigarettes": Nicotine delivery profile and cardiovascular and subjective effects. Cancer Epidemiol Biomarkers Prev. 19(8):1945-53 (2010).

Zhang, et al., In vitro particle size distributions in electronic and conventional cigarette aerosols suggest comparable deposition patterns. Nicotine Tob Res. 15(2):501-8 (2013).

Communication Relating to the Results of the Partial International Search for PCT/US2014/1039016, dated Aug. 26, 2014 (7 pages).

Anonymous: Any interest in determining nicotine by DVAP. Nov. 9, 2009.

PCT/US2014/037019 Third Party Observations and Comments filed on Sep. 1, 2015.

International Search Report and Written Opinion dated Apr. 27, 2015 for PCT Application No. PCT/US2014/072230.

\* cited by examiner

NICOTINE SALT FORMULATIONS FOR AEROSOL DEVICES AND METHODS THEREOF

CROSS REFERENCE

This application is a continuation of U.S. patent application Ser. No. 14/271,071, filed May 6, 2014, which claims the benefit of U.S. Provisional Patent Application Ser. No. 61/820,128, filed May 6, 2013, and U.S. Provisional Patent Application Ser. No. 61/912,507, filed Dec. 5, 2013, all of which are incorporated herein by reference in their entirety.

SUMMARY OF THE INVENTION

Provided herein is a method of delivering nicotine to a user comprising operating an electronic cigarette to a user wherein the electronic cigarette comprises a nicotine salt formulation comprising a nicotine salt in a biologically acceptable liquid carrier wherein an acid used to form said nicotine salt is characterized by vapor pressure >20 mmHg at 200° C., and inhaling an aerosol generated from the nicotine salt formulation heated by the electronic cigarette.

Provided herein is a method of delivering nicotine to a user comprising operating an electronic cigarette to a user wherein the electronic cigarette comprises a nicotine salt formulation comprising a nicotine salt in a biologically acceptable liquid carrier wherein an acid used to form said nicotine salt is characterized by vapor pressure of about 20 to 200 mmHg at 200° C., and inhaling an aerosol generated from the nicotine salt formulation heated by the electronic cigarette.

Provided herein is a method of delivering nicotine to a user comprising operating an electronic cigarette wherein the electronic cigarette comprises a nicotine salt formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point, and inhaling an aerosol generated from the nicotine salt formulation heated by the electronic cigarette.

Provided herein is a method of delivering nicotine to a user comprising providing an electronic cigarette to a user wherein the electronic cigarette comprises a nicotine salt formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point, and inhaling an aerosol generated from the nicotine salt formulation heated by the electronic cigarette.

Provided herein is a method of delivering nicotine to the blood of a user, said method comprising providing an aerosol that is inhaled by the user from an electronic cigarette that comprises a nicotine salt formulation wherein providing the aerosol comprises the electronic cigarette heating the formulation thereby generating the aerosol, wherein the aerosol is effective in delivering a level of nicotine in the blood of the user that is at least 5 ng/mL at about 1.5 minutes after a first puff of ten puffs of the aerosol, each puff taken at 30 second intervals.

Provided herein is a nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is characterized by vapor pressure >20 mmHg at 200° C.

Provided herein is a nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is characterized by vapor pressure of about 20 to 200 mmHg at 200° C.

Provided herein is a nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

Provided herein is a nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

Provided herein is a nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is characterized by vapor pressure >20 mmHg at 200° C.

Provided herein is a nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is characterized by vapor pressure of about 20 to 200 mmHg at 200° C.

Provided herein is a nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

Provided herein is a nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

Provided herein is a nicotine salt liquid formulation for use in an electronic cigarette the nicotine salt liquid formulation comprising a nicotine salt in a biologically acceptable liquid carrier wherein an acid used to form said nicotine salt is characterized by vapor pressure >20 mmHg at 200° C.

Provided herein is a nicotine salt liquid formulation for use in an electronic cigarette the nicotine salt liquid formulation comprising a nicotine salt in a biologically acceptable liquid carrier wherein an acid used to form said nicotine salt is characterized by vapor pressure of about 20 to 200 mmHg at 200° C.

Provided herein is a nicotine salt liquid formulation for use in an electronic cigarette the nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

Provided herein is a nicotine salt liquid formulation for use in an electronic cigarette the nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

Provided herein is a use of a nicotine salt formulation for delivery of nicotine to a user from an electronic cigarette wherein the nicotine salt formulation comprises a nicotine salt in a biologically acceptable liquid carrier wherein an acid used to form said nicotine salt is characterized by vapor pressure >20 mmHg at 200° C., and the nicotine salt formulation is heated by the electronic cigarette to generate an aerosol inhalable by the user.

Provided herein is a use of a nicotine salt formulation for delivery of nicotine to a user from an electronic cigarette wherein the nicotine salt formulation comprises a nicotine salt in a biologically acceptable liquid carrier wherein an acid used to form said nicotine salt is characterized by vapor pressure of about 20 to 200 mmHg at 200° C., and the nicotine salt formulation is heated by the electronic cigarette to generate an aerosol inhalable by the user.

Provided herein is a use of a nicotine salt formulation for delivery of nicotine to a user from an electronic cigarette wherein the nicotine salt formulation comprises a nicotine salt in a biologically acceptable liquid carrier wherein an acid used to form said nicotine salt is further characterized by a melting point <160° C., a boiling point >160° C., and at least a 50-degree difference between the melting point and the boiling point, and the nicotine salt formulation is heated by the electronic cigarette to generate an aerosol inhalable by the user.

Provided herein is a use of a nicotine salt formulation for delivery of nicotine to the blood of a user from an electronic cigarette, wherein the nicotine salt formulation in the electronic cigarette is heated to form an aerosol which delivers a level of nicotine in the blood of the user that is at least 5 ng/mL at about 1.5 minutes after a first puff of ten puffs of the aerosol, each puff taken at 30 second intervals.

Provided herein is a use of a nicotine salt formulation for delivery of nicotine to a user from an electronic cigarette wherein the nicotine salt formulation comprises a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point, and the nicotine salt formulation is heated by the electronic cigarette to generate an aerosol inhalable by the user.

Provided herein is a cartomizer for an electronic cigarette comprising:
a nicotine salt liquid formulation comprising a nicotine salt in a biologically acceptable liquid carrier wherein an acid used to form said nicotine salt is characterized by vapor pressure >20 mmHg at 200° C.;
an atomizer comprising a heating element in fluid communication with the nicotine salt liquid formulation; and
a fluid storage compartment that stores the nicotine salt liquid formulation.

Provided herein is a cartomizer for an electronic cigarette comprising:
a nicotine salt liquid formulation comprising a nicotine salt in a biologically acceptable liquid carrier wherein an acid used to form said nicotine salt is characterized by vapor pressure of about 20 to 200 mmHg at 200° C.;
an atomizer comprising a heating element in fluid communication with the nicotine salt liquid formulation; and
a fluid storage compartment that stores the nicotine salt liquid formulation.

Provided herein is a cartomizer for an electronic cigarette comprising:
a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
an atomizer comprising a heating element in fluid communication with the nicotine salt liquid formulation; and
a fluid storage compartment that stores the nicotine salt liquid formulation.

Provided herein is a cartomizer for an electronic cigarette comprising:
a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
an atomizer comprising a heating element in fluid communication with the nicotine salt liquid formulation; and
a fluid storage compartment that stores the nicotine salt liquid formulation.

Provided herein is an electronic cigarette for generating an inhalable aerosol comprising:
a fluid storage compartment;
a heater; and
a nicotine salt liquid formulation in the fluid storage compartment, the liquid formulation comprising a nicotine salt in a biologically acceptable liquid carrier wherein an acid used to form said nicotine salt is characterized by vapor pressure >20 mmHg at 200° C.;
a battery; and
a mouthpiece.

Provided herein is an electronic cigarette for generating an inhalable aerosol comprising:
a fluid storage compartment;
a heater; and
a nicotine salt liquid formulation in the fluid storage compartment, the liquid formulation comprising a nicotine salt in a biologically acceptable liquid carrier wherein an acid used to form said nicotine salt is characterized by vapor pressure of about 20 to 200 mmHg at 200° C.;
a battery; and
a mouthpiece.

Provided herein is an electronic cigarette for generating an inhalable aerosol comprising:
a fluid storage compartment;
a heater; and
a nicotine salt liquid formulation in the fluid storage compartment, the liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
a battery; and
a mouthpiece.

Provided herein is an electronic cigarette for generating an inhalable aerosol comprising:
a fluid storage compartment;
a heater; and
a nicotine salt liquid formulation in the fluid storage compartment, the liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
a battery; and
a mouthpiece.

Provided herein is a cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure >20 mmHg at 200° C.

Provided herein is a cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure of about 20 to 200 mmHg at 200° C.

Provided herein is a cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

Provided herein is a cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

Provided herein is a kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure >20 mmHg at 200° C.;
  iii. a heater;
  iv. a battery; and
  v. a mouthpiece; and
(b) instructions for using the electronic cigarette to generate an inhalable aerosol.

Provided herein is a kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure of about 20 to 200 mmHg at 200° C.;
  iii. a heater;
  iv. a battery; and
  v. a mouthpiece; and
(b) instructions for using the electronic cigarette to generate an inhalable aerosol.

Provided herein is a kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
  iii. a heater;
  iv. a battery; and
  v. a mouthpiece; and
(b) instructions for using the electronic cigarette to generate an inhalable aerosol.

Provided herein is a kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
  iii. a heater;
  iv. a battery; and
  v. a mouthpiece; and
(b) instructions for using the electronic cigarette to generate an inhalable aerosol.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are used, and the accompanying drawings of which.

DETAILED DESCRIPTION OF THE INVENTION

Figure 1:
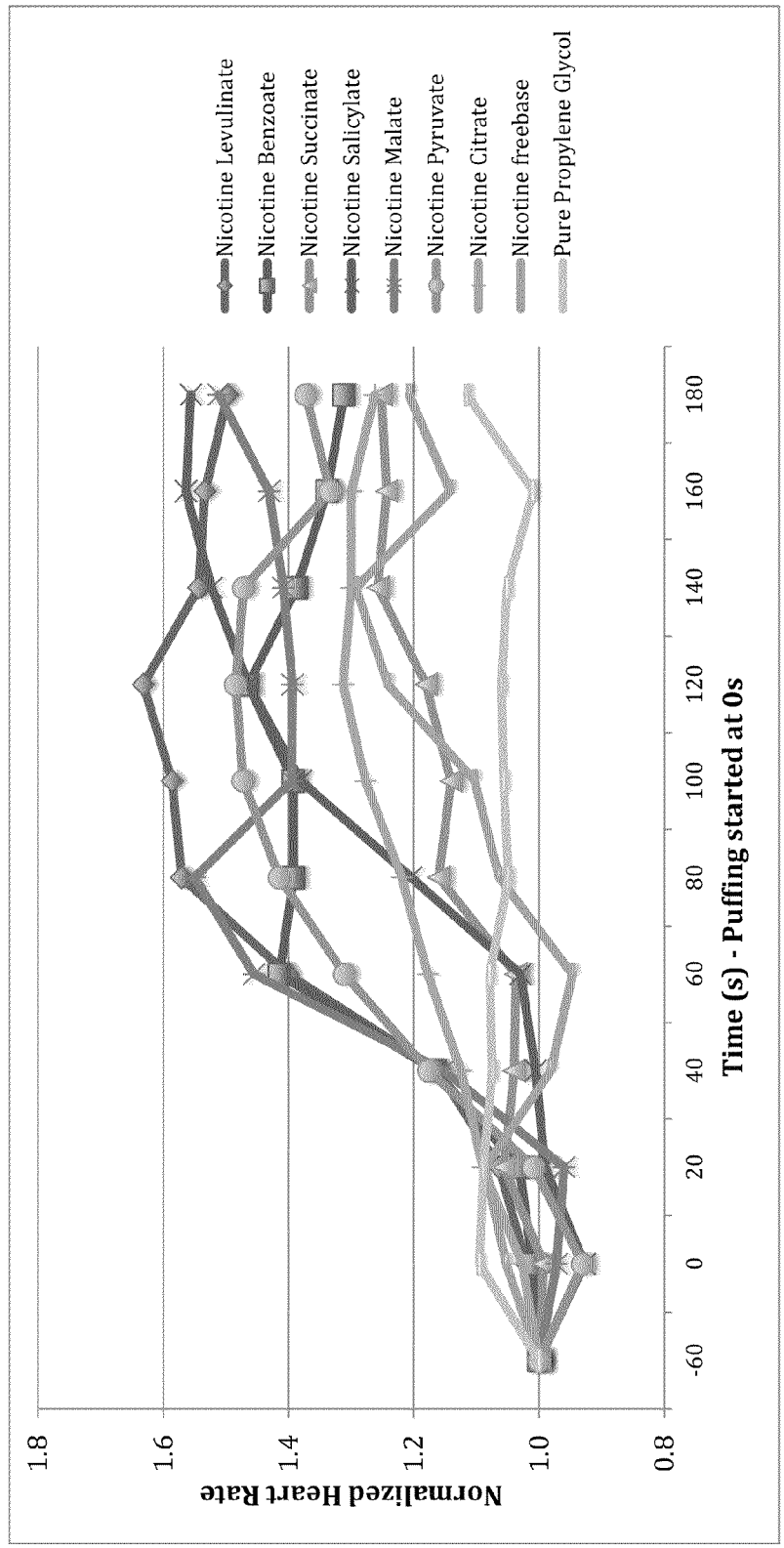
FIG. 1 illustrates results of heart rate data measured for six minutes from start of puffing. Y-axis is heart rate (bpm) and X-axis represent duration of the test (−60 to 180 seconds)

Nicotine is a chemical stimulant and increases heart rate and blood pressure when provided to an individual or animal. Nicotine transfer to an individual is associated with a feeling of physical and/or emotional satisfaction. Conflicting reports have been published regarding the transfer efficiency of free base nicotine in comparison to mono- or di-protonated nicotine salts. Studies on the transfer efficiency of free base nicotine and nicotine salts are complex and have yielded unpredictable results. Further, such transfer efficiency studies have been performed under extremely high temperature conditions, comparable to smoking; therefore, they offer scant guidance on the transfer efficiency of free base nicotine and nicotine salts under low-temperature vaporization conditions. Some reports have posited that nicotine free base should give rise to a greater satisfaction in a user than any corresponding nicotine salt.

It has been unexpectedly discovered herein that certain nicotine salt formulations provide satisfaction in an individual superior to that of free base nicotine, and more comparable to the satisfaction in an individual smoking a traditional cigarette. The satisfaction effect is consistent with an efficient transfer of nicotine to the lungs of an individual and a rapid rise of nicotine absorption in the plasma as shown, for non-limiting example, in Example 8, at least. It has also been unexpectedly discovered herein that certain nicotine salt formulations provide greater satisfaction than other nicotine salt formulations, and such effect has been shown in blood plasma levels of example nicotine salt formulations herein, for non-limiting example, in Example 8, at least. These results show a difference in rate of nicotine uptake in the blood that is higher for some nicotine salt formulations aerosolized by an electronic cigarette than for other nicotine salt formulations, and likewise higher than nicotine freebase formulations, while the peak concentration of the nicotine in the blood and total amount of nicotine delivered appears comparable to a traditional cigarette, and do not appear to vary significantly between the various nicotine formulations. Therefore, described herein are nicotine salt formulations for use in an electronic cigarette, or the like, that provide a general satisfaction effect consistent with an efficient transfer of nicotine to the lungs of an individual and a rapid rise of nicotine absorption in the plasma. Provided herein, therefore, are devices, formulation of nicotine salts, systems, cartomizers, kits and methods that are used to inhale an aerosol generated from a nicotine salt liquid formulation through the mouth or nose as described herein or as would be obvious to one of skill in the art upon reading the disclosure herein.

Consistent with these satisfaction effects, it has unexpectedly been found herein that there is a difference between the $C_{max}$ (maximum concentration) and $T_{max}$ (time at which the maximum concentration is measured) when measuring blood plasma nicotine levels of freebase nicotine formulations inhaled using a low temperature vaporization device, i.e. electronic cigarette, as compared to the $C_{max}$ and $T_{max}$ (similarly measuring blood plasma nicotine levels) of a traditional cigarette. Also consistent with these satisfaction effects, it has unexpectedly been found herein that there is a difference between the $C_{max}$ (maximum concentration) and $T_{max}$ (time at which the maximum concentration is measured) when measuring blood plasma nicotine levels of freebase nicotine formulations inhaled using a low temperature vaporization device, i.e. electronic cigarette, as compared to the $C_{max}$ and $T_{max}$ (similarly measuring blood plasma nicotine levels) of nicotine salt formulations inhaled using a low temperature vaporization device, i.e. electronic cigarette. Additionally, it has unexpectedly been found that there is a difference between the rate of nicotine uptake in the plasma of users inhaling freebase nicotine formulations using a low temperature vaporization device, i.e. electronic cigarette, as compared to the rate of nicotine uptake in the plasma of users inhaling smoke of a traditional cigarette. Furthermore, it has unexpectedly been found that there is a difference between the rate of nicotine uptake in the plasma of users inhaling freebase nicotine formulations using a low temperature vaporization device, i.e. electronic cigarette, as compared to the rate of nicotine uptake in the plasma of users inhaling nicotine salt formulations using a low temperature vaporization device, i.e. electronic cigarette.

Thus, looking at freebase nicotine as a source of nicotine in compositions used in e-cigarettes, freebase nicotine compositions' delivery of nicotine to blood when inhaled using is not necessarily comparable in blood plasma levels ($C_{max}$ and $T_{max}$) to a traditional cigarette's nicotine delivery to blood when inhaled. Freebase nicotine compositions' delivery of nicotine to blood when inhaled using is not necessarily comparable in blood plasma levels ($C_{max}$ and $T_{max}$) to nicotine salt formulations' nicotine delivery to blood when inhaled. Freebase nicotine compositions' delivery of nicotine to blood when inhaled using is not necessarily comparable in blood plasma levels when measuring the rate of nicotine uptake in the blood within the first 0-5 minutes to a traditional cigarette's nicotine delivery to blood when inhaled. Freebase nicotine compositions' delivery of nicotine to blood when inhaled using necessarily is not comparable in blood plasma levels when measuring the rate of nicotine uptake in the blood within the first 0-5 minutes to nicotine salt formulations' nicotine delivery to blood when inhaled.

Also consistent with these satisfaction effects, it has unexpectedly been found herein that while there appears to be comparable $C_{max}$ and $T_{max}$ values (measuring blood plasma nicotine levels) of nicotine salt formulations inhaled using a low temperature vaporization device, i.e. electronic cigarette, as compared to the $C_{max}$ and $T_{max}$ (similarly measuring blood plasma nicotine levels) of a traditional cigarette, there is a demonstrable difference between the rate of nicotine uptake in the plasma of users inhaling certain nicotine salt formulations using a low temperature vaporization device, i.e. electronic cigarette, as compared to the rate of nicotine uptake in the plasma of users inhaling other nicotine salt formulations using a low temperature vaporization device, i.e. electronic cigarette. It is also unexpected that while the $C_{max}$ and $T_{max}$ values are comparable to those of a traditional cigarette, (or are approaching that of a traditional cigarette), the rate of nicotine uptake in the plasma of blood of users is higher in certain nicotine salt formulations than that of the traditional cigarette. The nicotine salt formulations which demonstrate the quickest rate of nicotine uptake in the plasma were more preferred in satisfaction evaluations, and were rated more equivalent to cigarette satisfaction than the nicotine salt formulations showing the slowest rates of rise of nicotine in the subjects' blood plasma. In addition, doubling the concentration of the nicotine salt in the formulation may not necessarily impact the rate of absorption of nicotine in the blood (see, for non-limiting Example 8, nicotine benzoate tested in 4% and 2% concentrations).

Thus, looking at nicotine salt formulations used in e-cigarettes, nicotine salt formulations delivered using an e-cigarette appear comparable in $C_{max}$ and $T_{max}$ values (measuring blood plasma nicotine levels), however, not all nicotine salts perform similarly to each other or to a traditional cigarette with respect to the rate of nicotine uptake in the blood at early time periods (0-1.5 minutes). These results are unexpected. Nicotine salt formulations made using acids having a Vapor Pressure between 20-300 mmHg @ 200° C., or Vapor Pressure >20 mmHg @ 200° C., or a Vapor Pressure from 20 to 300 mmHg @ 200° C., or a Vapor Pressure from 20 to 200 mmHg @ 200° C., a Vapor Pressure between 20 and 300 mmHg @ 200° C. appear to have a higher rate of nicotine uptake in the blood at early time periods (0-1.5 minutes, 0-3 minutes, 0-2 minutes, 0-4 minutes for non-limiting example) than other nicotine salt formulations, however, they also provide satisfaction comparable to a traditional cigarette or closer to a traditional cigarette (as compared to other nicotine salt formulations or as compared to nicotine freebase formulations). For non-limiting example, acids that meet one or more criteria of the prior sentence include salicylic acid, sorbic acid, benzoic acid, lauric acid, and levulinic acid. Nicotine salt formulations made using acids that have a difference between boiling point and melting point of at least 50° C., and a boiling point greater than 160° C., and a melting point less than 160° C. appear to have a higher rate of nicotine uptake in the blood at early time periods (0-1.5 minutes, 0-3 minutes, 0-2 minutes, 0-4 minutes for non-limiting example) than other nicotine salt formulations, however, they also provide satisfaction comparable to a traditional cigarette or closer to a traditional cigarette (as compared to other nicotine salt formulations or as compared to nicotine freebase formulations). For non-limiting example, acids that meet the criteria of the prior sentence include salicylic acid, sorbic acid, benzoic acid, pyruvic acid, lauric acid, and levulinic acid. Nicotine salt formulations made using acids that have a difference between boiling point and melting point of at least 50° C., and a boiling point at most 40° C. less than operating temperature, and a melting point at least 40° C. lower than operating temperature appear to have a higher rate of nicotine uptake in the blood at early time periods (0-1.5 minutes, 0-3 minutes, 0-2 minutes, 0-4 minutes for non-limiting example) than other nicotine salt formulations, however, they also provide satisfaction comparable to a traditional cigarette or closer to a traditional cigarette (as compared to other nicotine salt formulations or as compared to nicotine freebase formulations). Operating temperature can be 100° C. to 300° C., or about 200° C., about 150° C. to about 250° C., 180 C to 220° C., about 180° C. to about 220° C., 185° C. to 215° C., about 185° C. to about 215° C., about 190° C. to about 210° C., 190° C. to 210° C., 195° C. to 205° C., or about 195° C. to about 205° C. For non-limiting example, acids that meet the criteria of the prior sentence include salicylic acid, sorbic acid, benzoic acid, pyruvic acid, lauric acid, and levulinic acid. Combinations of these criteria for preference of certain nicotine salt formulations are contemplated herein.

Other reasons for excluding certain acids from formulations may be unrelated to the rate of nicotine uptake, however. For example, an acid may be inappropriate for use with the device materials (corrosive or otherwise incompatible). Sulfuric acid is an example of this, which may be inappropriate for the e-cigarette device. An acid may be inappropriate for use in inhalation or for toxicity reasons—thus not be compatible for human consumption, ingestion, or inhalation. Sulfuric acid again is an example of this, which may be inappropriate for a user of an e-cigarette device, depending on the embodiment of the composition. An acid that is bitter or otherwise bad-tasting may also provide a reason for exclusion, such as acetic acid in some embodiments. Acids that oxidize at room temperature or at operating temperature may be inappropriate for certain embodiments, for example, sorbic acid, as this indicates a decomposition or reaction or instability that may be undesirable in the formulation. Decomposition of acids at room or operating temperatures may also indicate that the acid is inappropriate for use in the embodiment formulations. For example, citric acid decomposes at 175° C., and malic acid decomposes at 140° C., thus for a device operating at 200° C., these acids may not be appropriate. Acids that have poor solubility in the composition constituents may be inappropriate for use in certain embodiments of the compositions herein. For example, nicotine bitartrate with a composition of nicotine and tartaric acid as 1:2 molar ratio will not produce a solution at a concentration of 0.5%(w/w) nicotine or higher and 0.9%(w/w) tartaric acid or higher in propylene glycol (PG) or vegetable glycerin (VG) or any mixture of PG and VG at ambient conditions. As used herein, weight percentage (w/w) refers to the weight of the individual component over the weight of the total formulation.

As used in this specification and the claims, the singular forms "a," "an," and "the" include plural referents unless the context clearly dictates otherwise.

The term "organic acid" as used herein, refers to an organic compound with acidic properties (e.g., by Brønsted-Lowry definition, or Lewis definition). A common organic acid is the carboxylic acids, whose acidity is associated with their carboxyl group —COOH. A dicarboxylic acid possesses two carboxylic acid groups. The relative acidity of an organic is measured by its $pK_a$ value and one of skill in the art knows how to determine the acidity of an organic acid based on its given pKa value. The term "keto acid" as used herein, refers to organic compounds that contain a carboxylic acid group and a ketone group. Common types of keto acids include alpha-keto acids, or 2-oxoacids, such as pyruvic acid or oxaloacetic acid, having the keto group adjacent to the carboxylic acid; beta-keto acids, or 3-oxoacids, such as acetoacetic acid, having the ketone group at the second carbon from the carboxylic acid; gamma-keto acids, or 4-oxoacids, such as levulinic acid, having the ketone group at the third carbon from the carboxylic acid.

The term "electronic cigarette" or "e-cigarette" or "low temperature vaporization device" as used herein, refers to an electronic inhaler that vaporizes a liquid solution into an aerosol mist, simulating the act of tobacco smoking. The liquid solution comprises a formulation comprising nicotine. There are many electronic cigarettes which do not resemble conventional cigarettes at all. The amount of nicotine contained can be chosen by the user via the inhalation. In general, an electronic cigarette contains three essential components: a plastic cartridge that serves as a mouthpiece and a reservoir for liquid, an "atomizer" that vaporizes the liquid, and a battery. Other embodiment electronic cigarettes include a combined atomizer and reservoir, called a "cartomizer" that may or may not be disposable, a mouthpiece that may be integrated with the cartomizer or not, and a battery.

As used in this specification and the claims, unless otherwise stated, the term "about" refers to variations of 1%, 2%, 3%, 4%, 5%, 10%, 15%, or 25%, depending on the embodiment.

Suitable carriers (e.g., a liquid solvent) for the nicotine salts described herein include a medium in which a nicotine salt is soluble at ambient conditions, such that the nicotine salt does not form a solid precipitate. Examples include, but are not limited to, glycerol, propylene glycol, trimethylene glycol, water, ethanol and the like, as well as combinations thereof. In some embodiments, the liquid carrier comprises 0% to 100% of propylene glycol and 100% to 0% of vegetable glycerin. In some embodiments, the liquid carrier comprises 10% to 70% of propylene glycol and 90% to 30% of vegetable glycerin. In some embodiments, the liquid carrier comprises 20% to 50% of propylene glycol and 80% to 50% of vegetable glycerin. In some embodiments, the liquid carrier comprises 30% propylene glycol and 70% vegetable glycerin.

The formulations described herein vary in concentration. In some formulations, a dilute concentration of the nicotine salt in the carrier is utilized. In some formulations, a less dilute concentration of the nicotine salt in the carrier is utilized. In some formulations the concentration of nicotine in the nicotine salt formulation is about 1% (w/w) to about 25% (w/w). In some formulations the concentration of nicotine in the nicotine salt formulation is about 1% (w/w) to about 20% (w/w). In some formulations the concentration of nicotine in the nicotine salt formulation is about 1% (w/w) to about 18% (w/w). In some embodiments the concentration of nicotine in the nicotine salt formulation is about 1% (w/w) to about 15% (w/w). In some formulations the concentration of nicotine in the nicotine salt formulation is about 4% (w/w) to about 12% (w/w). In some formulations the concentration of nicotine in the nicotine salt formulation is about 4% (w/w). In some embodiments the concentration of nicotine in the nicotine salt formulation is about 2% (w/w). In some formulations the concentration of nicotine in the nicotine salt formulation is 1% (w/w) to 25% (w/w). In some formulations the concentration of nicotine in the nicotine salt formulation is 1% (w/w) to 20% (w/w). In some formulations the concentration of nicotine in the nicotine salt formulation is 1% (w/w) to 18% (w/w). In some formulations the concentration of nicotine in the nicotine salt formulation is 1% (w/w) to 15% (w/w). In some formulations the concentration of nicotine in the nicotine salt formulation is 4% (w/w) to 12% (w/w). In some formulations the concentration of nicotine in the nicotine salt formulation is 4% (w/w). In some formulations the concentration of nicotine in the nicotine salt formulation is 2% (w/w). In some formulations, a less dilute concentration of one nicotine salt is used in conjunction with a more dilute concentration of a second nicotine salt. In some formulations, the concentration of nicotine in the first nicotine salt formulation is about 1% to about 20%, and is combined with a second nicotine salt formulation having a concentration of nicotine therein from about 1% to about 20% or any range or concentration therein. In some formulations, the concentration of nicotine in the first nicotine salt formulation is 1% to 20%, and is combined with a second nicotine salt formulation having a concentration of nicotine therein from 1% to 20% or any range or concentration therein. As used with respect to concentrations of nicotine in the nicotine salt formulations, the term "about" refers to ranges of 0.05% (i.e. if the concentration is about 2%, the range is 1.95%-2.05%), 0.1 (i.e. if the concentration is about 2%, the range is 1.9%-2.1%), 0.25 (i.e. if the concentration is about 2%, the range is 1.75%-2.25%), 0.5 (i.e. if the concentration is about 2%, the range is 1.5%-2.5%), or 1 (i.e. if the concentration is about 4%, the range is 3%-5%), depending on the embodiment.

Nicotine salts are formed by the addition of a suitable acid, including organic or inorganic acids. In some formulations provided herein, suitable organic acids are carboxylic acids. Examples of organic carboxylic acids disclosed herein are monocarboxylic acids, dicarboxylic acids (organic acid containing two carboxylic acid groups), carboxylic acids containing an aromatic group such as benzoic acids, hydroxycarboxylic acids, heterocyclic carboxylic acids, terpenoid acids, sugar acids; such as the pectic acids, amino acids, cycloaliphatic acids, aliphatic carboxylic acids, keto carboxylic acids, and the like. In some formulations provided herein, the organic acids used herein are monocarboxylic acids. Nicotine salts are formed from the addition of a suitable acid to nicotine. In some formulations provided herein, the stoichiometric ratios of the nicotine to acid (nicotine:acid) are 1:1, 1:2, 1:3, 1:4, 2:3, 2:5, 2:7, 3:4, 3:5, 3:7, 3:8, 3:10, 3:11, 4:5, 4:7, 4:9, 4:10, 4:11, 4:13, 4:14, 4:15, 5:6, 5:7, 5:8, 5:9, 5:11, 5:12, 5:13, 5:14, 5:16, 5:17, 5:18, or 5:19. In some formulations provided herein, the stoichiometric ratios of the nicotine to acid are 1:1, 1:2, 1:3, or 1:4 (nicotine:acid).

Nicotine is an alkaloid molecule that comprises two basic nitrogens. It may occur in different states of protonation. For example, if no protonation exists, nicotine is referred to as the "free base." If one nitrogen is protonated, then the nicotine would be "mono-protonated."

Nicotine salt formulations may be formed by adding a suitable acid to nicotine, stirring the neat mixture at ambient temperature or at elevated temperature, and then diluting the neat mixture with a carrier mixture, such as a mixture of propylene glycol and glycerin. In some embodiments, the suitable acid is completely dissolved by the nicotine prior to dilution. The suitable acid may not completely dissolved by the nicotine prior to dilution. The addition of the suitable acid to the nicotine to form a neat mixture may cause an exothermic reaction. The addition of the suitable acid to the nicotine to form a neat mixture may be conducted at 55° C. The addition of the suitable acid to the nicotine to form a neat mixture may be conducted at 90° C. The neat mixture may be cooled to ambient temperature prior to dilution. The dilution may be carried out at elevated temperature.

Nicotine salt formulations may be prepared by combining nicotine and a suitable acid in a carrier mixture, such as a mixture of propylene glycol and glycerin. The mixture of nicotine and a first carrier mixture is combined with a mixture of a suitable acid in a second carrier mixture. In some embodiments, the first and second carrier mixtures are identical in composition. In some embodiments, the first and second carrier mixtures are not identical in composition. In some embodiments, heating of nicotine/acid/carrier mixture is required to facilitate complete dissolution.

In some embodiments, nicotine salt formulations may be prepared and added to a solution of 3:7 ratio by weight of propylene glycol (PG)/vegetable glycerin (VG), and mixed thoroughly. While described herein as producing 10 g of each of the formulations, all procedures noted infra are scalable. Other manners of formulation may also be employed form the formulations noted infra, without departing from the disclosure herein, and as would be known to one of skill in the art upon reading the disclosure herein.

Figure 3:
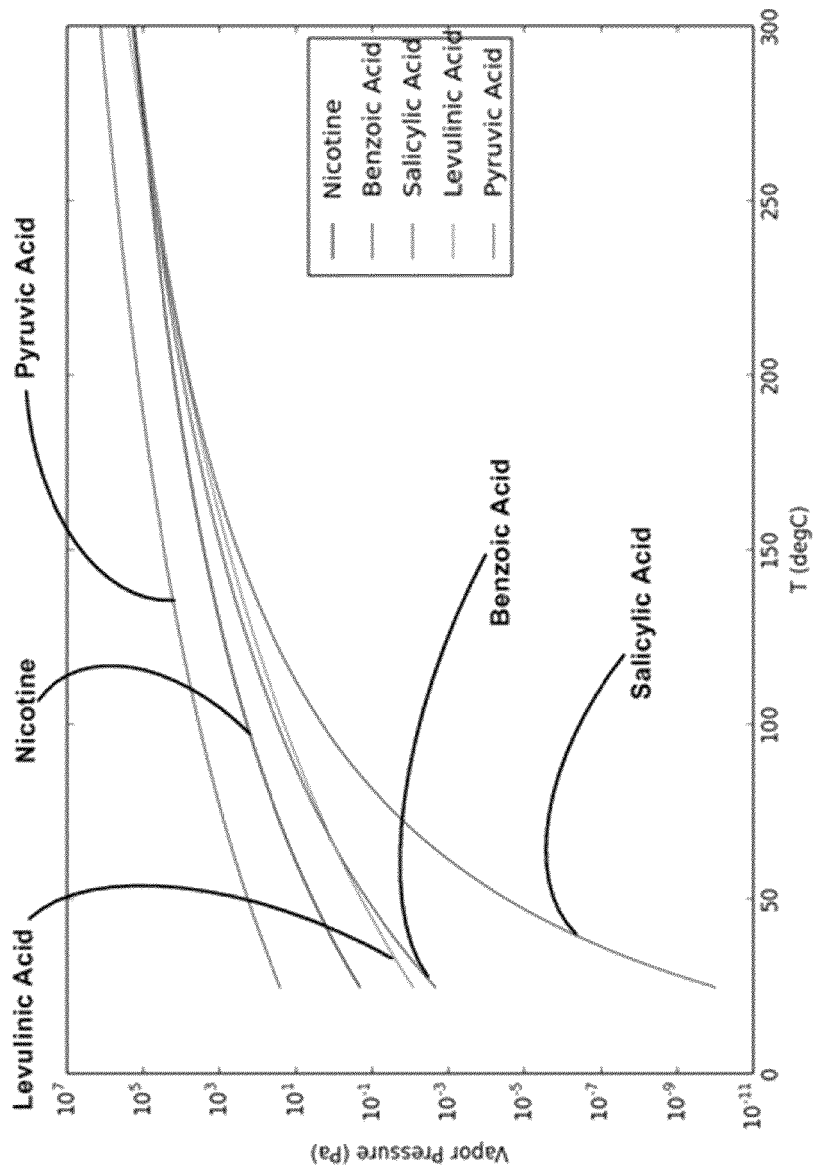
FIG. 3 illustrates the calculated vapor pressures of various acids relative to nicotine.

The optimal nicotine salt formulation may be determined by the vapor pressure of the constituent acid. In some embodiments, the nicotine salt formulations comprise an acid with a vapor pressure that is similar to the vapor pressure of free base nicotine. In some embodiments, the nicotine salt formulations are formed from an acid with a vapor pressure that is similar to the vapor pressure of free base nicotine at the heating temperature of the device. FIG. 3 illustrates this trend. Nicotine salts formed from nicotine and benzoic acid; nicotine and salicylic acid; or nicotine and levulinic acid are salts that produce a satisfaction in an individual user consistent with efficient transfer of nicotine and a rapid rise in nicotine plasma levels. This pattern may be due to the mechanism of action during heating of the nicotine salt formulation. The nicotine salt may disassociate at, or just below, the heating temperature of the device, resulting in a mixture of free base nicotine and the individual acid. At that point, if both the nicotine and acid have similar vapor pressures, they may aerosolize at the same time, giving rise to a transfer of both free base nicotine and the constituent acid to the user.

The nicotine salt liquid formulation for generating an inhalable aerosol upon heating in an electronic cigarette may comprise a nicotine salt in a biologically acceptable liquid carrier; wherein the acid used to form said nicotine salt is characterized by a vapor pressure between 20-4000 mmHg at 200° C. In some embodiments, the acid used to form the nicotine salt is characterized by vapor pressure between 20-2000 mmHg at 200° C. In some embodiments, the acid used to form the nicotine salt is characterized by vapor pressure between 100-300 mmHg at 200° C.

Unexpectedly, different nicotine salt formulations produced varying degrees of satisfaction in an individual. In some embodiments, the extent of protonation of the nicotine salt affected satisfaction, such that more protonation was less satisfying as compared to less protonation. The nicotine salt formed may be monoprotonated. The nicotine salt formed may be diprotonated. The nicotine salt may exist in more than one protonation state, e.g., an equilibrium of mono-protonated and di-protonated nicotine salts. The extent of protonation of the nicotine molecule may be dependent upon the stoichiometric ratio of nicotine:acid used in the salt formation reaction. The extent of protonation of the nicotine molecule may be dependent upon the solvent. The extent of protonation of the nicotine molecule may be unknown. In some embodiments, monoprotonated nicotine salts produced a high degree of satisfaction in the user. For example, nicotine benzoate and nicotine salicylate are mono-protonated nicotine salts and all produce a high degree of satisfaction in the user. The reason for this trend may be explained by a mechanism of action wherein the nicotine is first deprotonated prior to transfer to the vapor with the constituent acid and then retained and stabilized after re-protonated by the acid going down stream to the lungs of the user. It may be easier to remove one proton versus two protons, thus resulting in better transfer efficiency. In addition, the lack of satisfaction of free base nicotine indicates that a second factor may be important. A nicotine salt may be best performing when it is at its optimal extent of protonation, depending on the salt. For example, nicotine pyruvate is a nicotine salt with 1:2 nicotine:acid ratio. The formulation containing nicotine pyruvate (1:2) may deliver more satisfaction to the user than the one containing same amount of nicotine but only half amount of pyruvic acid, i.e. nicotine pyruvate (1:1). This may be explained as 1 mole of nicotine produces a salt with 2 moles of pyruvic acid. When there is not enough pyruvic acid to associate with all nicotine molecules, the free base nicotine left unprotonated in the formulation may reduce the satisfaction the formulation provides.

The flavor of the constituent acid used in the salt formation may be a consideration in choosing the acid. A suitable acid may have minimal or no toxicity to humans in the concentrations used. A suitable acid may be compatible with the electronic cigarette components it contacts or could contact at the concentrations used. That is, such acid does not degrade or otherwise react with the electronic cigarette components it contacts or could contact. The odor of the constituent acid used in the salt formation may be a consideration in choosing a suitable acid. The concentration of the nicotine salt in the carrier may affect the satisfaction in the individual user. In some embodiments, the flavor of the formulation is adjusted by changing the acid. In some embodiments, the flavor of the formulation is adjusted by adding exogenous flavorants. In some embodiments, an unpleasant tasting or smelling acid is used in minimal quantities to mitigate such characteristics. In some embodiments, exogenous pleasant smelling or tasting acid is added to the formulation. Examples of salts which can provide flavor and aroma to the mainstream aerosol at certain levels include nicotine acetate, nicotine oxalate, nicotine malate, nicotine isovalerate, nicotine lactate, nicotine citrate, nicotine phenylacetate and nicotine myristate.

Nicotine salt formulations may generate an inhalable aerosol upon heating in an electronic cigarette. The amount of nicotine or nicotine salt aerosol inhaled may be user-determined. The user may, for example, modify the amount of nicotine or nicotine salt inhaled by adjusting his inhalation strength.

Formulations are described herein comprising two or more nicotine salts. In some embodiments, wherein a formulation comprises two or more nicotine salts, each individual nicotine salt is formed as described herein.

Nicotine salt formulations, as used herein, refer to a single or mixture of nicotine salts with other suitable chemical components used for e-cigarette, such as carriers, stabilizers, diluents, dispersing agents, suspending agents, thickening agents, and/or excipients. In certain embodiments, the nicotine salt formulation is stirred at ambient conditions for 20 minutes. In certain embodiments, the nicotine salt formulation is heated and stirred at 55 C for 20 minutes. In certain embodiments, the nicotine salt formulation is heated and stirred at 90 C for 60 minutes. In certain embodiments, the formulation facilitates administration of nicotine to an organism (e.g., lung).

The nicotine of nicotine salt formulations provided herein is either naturally occurring nicotine (e.g., from extract of nicotineous species such as tobacco), or synthetic nicotine. In some embodiments, the nicotine is (−)-nicotine, (+)-nicotine, or a mixture thereof. In some embodiments, the nicotine is employed in relatively pure form (e.g., greater than about 80% pure, 85% pure, 90% pure, 95% pure, or 99% pure). In some embodiments, the nicotine for nicotine salt formulation provided herein is "water clear" in appearance in order to avoid or minimize the formation of tarry residues during the subsequent salt formation steps.

Nicotine salt formulations used for e-cigarettes described herein, in some embodiments, have a nicotine concentration of about 0.5% (w/w) to about 20% (w/w), wherein the concentration is of nicotine weight to total solution weight, i.e. (w/w). In certain embodiments, nicotine salt formulations provided herein have a nicotine concentration of about 1% (w/w) to about 20% (w/w). In certain embodiments, nicotine salt formulations provided herein have a nicotine concentration of about 1% (w/w) to about 18% (w/w). In certain embodiments, nicotine salt formulations provided herein have a nicotine concentration of about 1% (w/w) to about 15% (w/w). In certain embodiments, nicotine salt formulations provided herein have a nicotine concentration of about 4% (w/w) to about 12% (w/w). In certain embodiments, nicotine salt formulations provided herein have a nicotine concentration of about 1% (w/w) to about 18% (w/w), about 3% (w/w) to about 15% (w/w), or about 4% (w/w) to about 12% (w/w). In certain embodiments, nicotine salt formulations provided herein have a nicotine concentration of about 0.5% (w/w) to about 10% (w/w). In certain embodiments, nicotine salt formulations provided herein have a nicotine concentration of about 0.5% (w/w) to about 5% (w/w). In certain embodiments, nicotine salt formulations provided herein have a nicotine concentration of about 0.5% (w/w) to about 4% (w/w). In certain embodiments, nicotine salt formulations provided herein have a nicotine concentration of about 0.5% (w/w) to about 3% (w/w). In certain embodiments, nicotine salt formulations provided herein have a nicotine concentration of about 0.5% (w/w) to about 2% (w/w). In certain embodiments, nicotine salt formulations provided herein have a nicotine concentration of about 0.5% (w/w) to about 1% (w/w). In certain embodiments, nicotine salt formulations provided herein have a nicotine concentration of about 1% (w/w) to about 10% (w/w). In certain embodiments, nicotine salt formulations provided herein have a nicotine concentration of about 1% (w/w) to about 5% (w/w). In certain embodiments, nicotine salt formulations provided herein have a nicotine concentration of about 1% (w/w) to about 4% (w/w). In certain embodiments, nicotine salt formulations provided herein have a nicotine concentration of about 1% (w/w) to about 3% (w/w). In certain embodiments, nicotine salt formulations provided herein have a nicotine concentration of about 1% (w/w) to about 2% (w/w). In certain embodiments, nicotine salt formulations provided herein have a nicotine concentration of about 2% (w/w) to about 10% (w/w). In certain embodiments, nicotine salt formulations provided herein have a nicotine concentration of about 2% (w/w) to about 5% (w/w). In certain embodiments, nicotine salt formulations provided herein have a nicotine concentration of about 2% (w/w) to about 4% (w/w). Certain embodiments provide a nicotine salt formulation having a nicotine concentration of about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15%, 16%, 17%, 18%, 19%, or 20% (w/w), or more, including any increments therein. Certain embodiments provide a nicotine salt formulation having a nicotine concentration of about 5% (w/w). Certain embodiments provide a nicotine salt formulation having a nicotine concentration of about 4% (w/w). Certain embodiments provide a nicotine salt formulation having a nicotine concentration of about 3% (w/w). Certain embodiments provide a nicotine salt formulation having a nicotine concentration of about 2% (w/w). Certain embodiments provide a nicotine salt formulation having a nicotine concentration of about 1% (w/w). Certain embodiments provide a nicotine salt formulation having a nicotine concentration of about 0.5% (w/w).

The formulation further may comprise one or more flavorants.

The suitable acid for the nicotine salt formulation may have a vapor pressure >20 mmHg at 200° C. and is non-corrosive to the electronic cigarette or is non-toxic to humans. In some embodiments, the suitable acid for nicotine salt formation is selected from the group consisting of salicylic acid, formic acid, sorbic acid, acetic acid, benzoic acid, pyruvic acid, lauric acid, and levulinic acid.

The suitable acid for the nicotine salt formulation may have a vapor pressure of about 20 to 200 mmHg at 200° C. and is non-corrosive to the electronic cigarette or is non-toxic to humans. In some embodiments, the suitable acid for nicotine salt formation is selected from the group consisting of salicylic acid, benzoic acid, lauric acid, and levulinic acid.

The suitable acid for the nicotine salt formulation may have a melting point <160° C., a boiling point >160° C., at least a 50-degree difference between the melting point and the boiling point, and is non-corrosive to the electronic cigarette or is non-toxic to humans. In some embodiments, the suitable acid for nicotine salt formation has a melting point at least 40 degrees lower than the operating temperature of the electronic cigarette, a boiling point no more than 40 degrees lower than the operating temperature of the electronic cigarette, at least a 50-degree difference between the melting point and the boiling point, and is non-corrosive to the electronic cigarette or is non-toxic to humans; wherein the operating temperature is 200° C. In some embodiments, the suitable acid for nicotine salt formation is selected from the group consisting of salicylic acid, sorbic acid, benzoic acid, pyruvic acid, lauric acid, and levulinic acid.

The suitable acid for the nicotine salt formulation does not decompose at the operating temperature of the electronic cigarette. In some embodiments, the suitable acid for nicotine salt formation does not oxidize at the operating temperature of the electronic cigarette. In some embodiments, the suitable acid for nicotine salt formation does not oxidize at room temperature. In some embodiments, the suitable acid for nicotine salt formation does not provide an unpleasant taste. In some embodiments, the suitable acid for nicotine salt formation has good solubility in a liquid formulation for use in an electronic cigarette.

Figure 7:
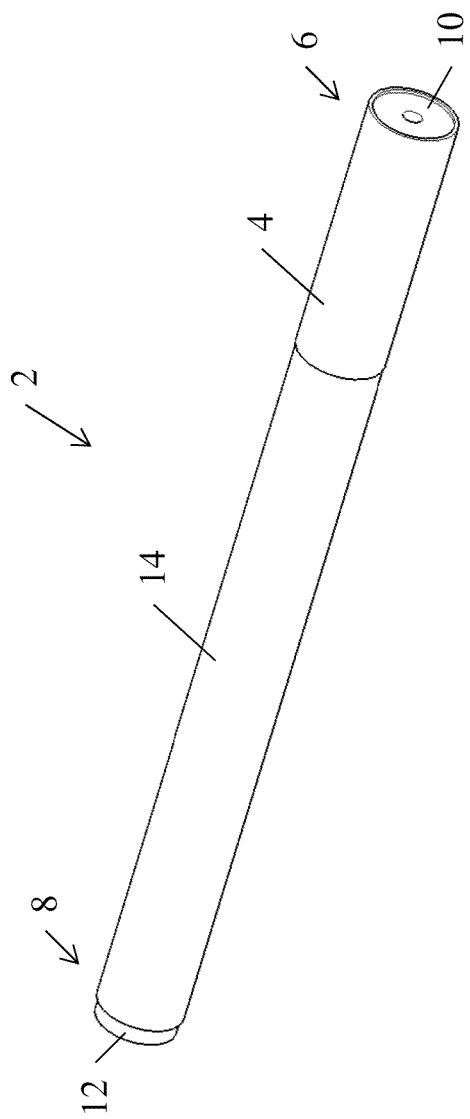
FIG. 7 depicts an example embodiment of an electronic cigarette having a fluid storage compartment comprising an embodiment nicotine salt formulation described herein.

Provided herein is an electronic cigarette 2 having a fluid storage compartment 4 comprising an embodiment nicotine salt formulation of any embodiment described herein within the fluid storage compartment described herein. An embodiment is shown in FIG. 7. The electronic cigarette 2 of FIG. 7 includes a mouth end 6, and a charging end 8. The mouth-end 6 includes a mouthpiece 10. The charging end 8 may connect to a battery or a charger or both, wherein the battery is within a body of the electronic cigarette, and the charger is separate from the battery and couples to the body or the battery to charge the battery. In some embodiments the electronic cigarette comprises a rechargeable battery within a body 14 of the electronic cigarette and the charge end 8 comprises a connection 12 for charging the rechargeable battery. In some embodiments, the electronic cigarette comprises a cartomizer that comprises the fluid storage compartment and an atomizer. In some embodiments, the atomizer comprises a heater. In some embodiments the fluid storage compartment 4 is separable from an atomizer. In some embodiments the fluid storage compartment 4 is replaceable as part of a replaceable cartridge. In some embodiments the fluid storage compartment 4 is refillable. In some embodiments, the mouthpiece 10 is replaceable.

Figure 8:
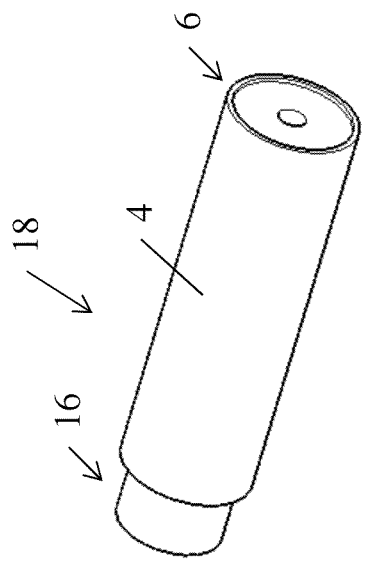
FIG. 8 depicts an example embodiment of an electronic cigarette cartomizer having a fluid storage compartment, a heater, and comprising an embodiment nicotine salt formulation described herein.

Provided herein is a cartomizer 18 for an electronic cigarette 2 having a fluid storage compartment 4 comprising an embodiment nicotine salt formulation of any embodiment described herein within the fluid storage compartment described herein. The cartomizer 18 embodiment of FIG. 8 includes a mouth end 6, and a connection end 16. The connection end 16 in the embodiment of FIG. 8 couples the cartomizer 14 to a body of an electronic cigarette, or to a battery of the electronic cigarette, or both. The mouth end 6 includes a mouthpiece 10. In some embodiments, the cartomizer does not include a mouthpiece, and in such embodiments, the cartomizer can be coupled to a mouthpiece of an electronic cigarette, or the cartomizer can be coupled to a battery or body of an electronic cigarette, while the mouthpiece is also coupled to the battery or the body of the electronic cigarette. In some embodiments, the mouthpiece is integral with the body of the electronic cigarette. In some embodiments, including the embodiment of FIG. 8, the cartomizer 18 comprises the fluid storage compartment 4 and an atomizer (not shown). In some embodiments, the atomizer comprises a heater (not shown)

EXAMPLES

Example 1

Preparation of Nicotine Salt Formulations

Various nicotine formulations were prepared and added to a solution of 3:7 ratio by weight of propylene glycol (PG)/vegetable glycerin (VG), and mixed thoroughly. The examples shown below were used to make 10 g of each of the formulations. All procedures are scalable.

For example, in order to make nicotine formulations with a final nicotine free base equivalent concentration of 2% (w/w), the following procedures were applied to each individual formulation.

Nicotine benzoate salt formulation: 0.15 g benzoic acid was added to a beaker followed by adding 0.2 g nicotine to the same beaker. The mixture was stirred at 55° C. for 20 minutes until benzoic acid was completely dissolved and an orange oily mixture was formed. The mixture was cooled down to ambient conditions. 9.65 g PG/VG (3:7) solution was added to the orange nicotine benzoate salt and the mixture was stirred until a visually homogenous formulation solution was achieved.

Nicotine benzoate salt formulation can also be made by adding 0.15 g benzoic acid to a beaker followed by adding 0.2 g nicotine and 9.65 g PG/VG (3:7) solution to the same beaker. The mixture was then stirred at 55° C. for 20 minutes until a visually homogenous formulation solution was achieved with no undissolved chemicals.

Nicotine citrate salt formulation was made by adding 0.47 g citric acid to a beaker followed by adding 0.2 g nicotine and 9.33 g PG/VG (3:7) solution to the same beaker. The mixture was then stirred at 90° C. for 60 minutes until a visually homogenous formulation solution was achieved with no undissolved chemicals.

Nicotine malate salt formulation was made by adding 0.33 g L-malic acid to a beaker followed by adding 0.2 g nicotine and 9.47 g PG/VG (3:7) solution to the same beaker. The mixture was then stirred at 90° C. for 60 minutes until a visually homogenous formulation solution was achieved with no undissolved chemicals.

Nicotine succinate salt formulation was made by adding 0.29 g succinic acid to a beaker followed by adding 0.2 g nicotine and 9.51 g PG/VG (3:7) solution to the same beaker. The mixture was then stirred at 90° C. for 60 minutes until a visually homogenous formulation solution was achieved with no undissolved chemicals.

Nicotine salicylate salt formulation was made by adding 0.17 g salicylic acid to a beaker followed by adding 0.2 g nicotine and 9.63 g PG/VG (3:7) solution to the same beaker. The mixture was then stirred at 90° C. for 60 minutes until a visually homogenous formulation solution was achieved with no undissolved chemicals.

Nicotine salicylate salt formulation can also be made by adding 0.17 g salicylic acid to a beaker followed by adding 0.2 g nicotine to the same beaker. The mixture was stirred at 90° C. for 60 minutes until salicylic acid was completely dissolved and an orange oily mixture was formed. The mixture was either cooled to ambient conditions or kept at 90° C. when 9.63 g PG/VG (3:7) solution was added. The mixture was then stirred at 90° C. until a visually homogenous formulation solution was achieved with no undissolved chemicals.

Nicotine free base formulation was made by adding 0.2 g nicotine to a beaker followed by adding 9.8 g PG/VG (3:7) solution to the same beaker. The mixture was then stirred at ambient conditions for 10 minutes until a visually homogenous formulation solution was achieved.

For example, in order to make nicotine salt formulations with a final nicotine free base equivalent concentration of 3% (w/w), the following procedures were applied to each individual formulation.

Nicotine benzoate salt formulation: 0.23 g benzoic acid was added to a beaker followed by adding 0.3 g nicotine to the same beaker. The mixture was stirred at 55° C. for 20 minutes until benzoic acid was completely dissolved and an orange oily mixture was formed. The mixture was cooled down to ambient conditions. 9.47 g PG/VG (3:7) solution was added to the orange nicotine benzoate salt and the blend was stirred until a visually homogenous formulation solution was achieved.

Nicotine benzoate salt formulation can also be made by adding 0.23 g benzoic acid to a beaker followed by adding 0.3 g nicotine and 9.47 g PG/VG (3:7) solution to the same beaker. The mixture was then stirred at 55° C. for 20 minutes until a visually homogenous formulation solution was achieved with no undissolved chemicals.

Nicotine citrate salt formulation was made by adding 0.71 g citric acid to a beaker followed by adding 0.3 g nicotine and 8.99 g PG/VG (3:7) solution to the same beaker. The mixture was then stirred at 90° C. for 60 minutes until a visually homogenous formulation solution was achieved with no undissolved chemicals.

Nicotine malate salt formulation was made by adding 0.5 g L-malic acid to a beaker followed by adding 0.3 g nicotine and 9.2 g PG/VG (3:7) solution to the same beaker. The mixture was then stirred at 90° C. for 60 minutes until a visually homogenous formulation solution was achieved with no undissolved chemicals.

Nicotine levulinate salt formulation was made by adding melted 0.64 g levulinic acid to a beaker followed by adding 0.3 g nicotine to the same beaker. The mixture was stirred at ambient conditions for 10 minutes. Exothermic reaction took place and oily product was produced. The mixture was allowed to cool down to ambient temperature and 9.06 g PG/VG (3:7) solution was added to the same beaker. The mixture was then stirred at ambient conditions for 20 minutes until a visually homogenous formulation solution was achieved.

Nicotine pyruvate salt formulation was made by adding 0.33 g pyruvic acid to a beaker followed by adding 0.3 g nicotine to the same beaker. The mixture was stirred at ambient conditions for 10 minutes. Exothermic reaction took place and oily product was produced. The mixture was allowed to cool down to ambient temperature and 9.37 g PG/VG (3:7) solution was added to the same beaker. The mixture was then stirred at ambient conditions for 20 minutes until a visually homogenous formulation solution was achieved.

Nicotine succinate salt formulation was made by adding 0.44 g succinic acid to a beaker followed by adding 0.3 g nicotine and 9.26 g PG/VG (3:7) solution to the same beaker. The mixture was then stirred at 90° C. for 60 minutes until a visually homogenous formulation solution was achieved with no undissolved chemicals.

Nicotine salicylate salt formulation was made by adding 0.26 g salicylic acid to a beaker followed by adding 0.3 g nicotine and 9.44 g PG/VG (3:7) solution to the same beaker. The mixture was then stirred at 90° C. for 60 minutes until a visually homogenous formulation solution was achieved with no undissolved chemicals.

Nicotine salicylate salt formulation can also be made by adding 0.26 g salicylic acid to a beaker followed by adding 0.3 g nicotine to the same beaker. The mixture was stirred at 90° C. for 60 minutes until salicylic acid was completely dissolved and an orange oily mixture was formed. The mixture was either cooled to ambient conditions or kept at 90° C. when 9.44 g PG/VG (3:7) solution was added. The blend was then stirred at 90 C until a visually homogenous formulation solution was achieved with no undissolved chemicals.

Nicotine free base formulation was made by adding 0.3 g nicotine to a beaker followed by adding 9.7 g PG/VG (3:7) solution to the same beaker. The mixture was then stirred at ambient conditions for 10 minutes until a visually homogenous formulation solution was achieved.

For example, in order to make nicotine salt formulations with a final nicotine free base equivalent concentration of 4% (w/w), the following procedures were applied to each individual formulation.

Nicotine benzoate salt formulation: 0.3 g benzoic acid was added to a beaker followed by adding 0.4 g nicotine to the same beaker. The mixture was stirred at 55° C. for 20 minutes until benzoic acid was completely dissolved and an orange oily mixture was formed. The mixture was cooled down to ambient conditions. 9.7 g PG/VG (3:7) solution was added to the orange nicotine benzoate salt and the blend was stirred until a visually homogenous formulation solution was achieved.

Nicotine benzoate salt formulation can also be made by adding 0.3 g benzoic acid to a beaker followed by adding 0.4 g nicotine and 9.7 g PG/VG (3:7) solution to the same beaker. The mixture was then stirred at 55° C. for 20 minutes until a visually homogenous formulation solution was achieved with no undissolved chemicals.

For example, in order to make nicotine salt formulations with a final nicotine free base equivalent concentration of 5% (w/w), the following procedures were applied to each individual formulation.

Nicotine benzoate salt formulation: 0.38 g benzoic acid was added to a beaker followed by adding 0.5 g nicotine to the same beaker. The mixture was stirred at 55° C. for 20 minutes until benzoic acid was completely dissolved and an orange oily mixture was formed. The mixture was cooled down to ambient conditions. 9.12 g PG/VG (3:7) solution was added to the orange nicotine benzoate salt and the blend was stirred until a visually homogenous formulation solution was achieved.

Nicotine benzoate salt formulation can also be made by adding 0.38 g benzoic acid to a beaker followed by adding 0.5 g nicotine and 9.12 g PG/VG (3:7) solution to the same beaker. The mixture was then stirred at 55° C. for 20 minutes until a visually homogenous formulation solution was achieved with no undissolved chemicals.

Nicotine malate salt formulation was made by adding 0.83 g L-malic acid to a beaker followed by adding 0.5 g nicotine and 8.67 g PG/VG (3:7) solution to the same beaker. The mixture was then stirred at 90° C. for 60 minutes until a visually homogenous formulation solution was achieved with no undissolved chemicals.

Nicotine levulinate salt formulation was made by adding melted 1.07 g levulinic acid to a beaker followed by adding 0.5 g nicotine to the same beaker. The mixture was stirred at ambient conditions for 10 minutes. Exothermic reaction took place and oily product was produced. The mixture was allowed to cool down to ambient temperature and 8.43 g PG/VG (3:7) solution was added to the same beaker. The mixture was then stirred at ambient conditions for 20 minutes until a visually homogenous formulation solution was achieved.

Nicotine pyruvate salt formulation was made by adding 0.54 g pyruvic acid to a beaker followed by adding 0.5 g nicotine to the same beaker. The mixture was stirred at ambient conditions for 10 minutes. Exothermic reaction took place and oily product was produced. The mixture was allowed to cool down to ambient temperature and 8.96 g PG/VG (3:7) solution was added to the same beaker. The mixture was then stirred at ambient conditions for 20 minutes until a visually homogenous formulation solution was achieved.

Nicotine succinate salt formulation was made by adding 0.73 g succinic acid to a beaker followed by adding 0.5 g nicotine and 8.77 g PG/VG (3:7) solution to the same beaker. The mixture was then stirred at 90° C. for 60 minutes until a visually homogenous formulation solution was achieved with no undissolved chemicals.

Nicotine salicylate salt formulation was made by adding 0.43 g salicylic acid to a beaker followed by adding 0.5 g nicotine and 9.07 g PG/VG (3:7) solution to the same beaker. The mixture was then stirred at 90° C. for 60 minutes until a visually homogenous formulation solution was achieved with no undissolved chemicals.

Nicotine salicylate salt formulation can also be made by adding 0.43 g salicylic acid to a beaker followed by adding 0.5 g nicotine to the same beaker. The mixture was stirred at 90° C. for 60 minutes until salicylic acid was completely dissolved and an orange oily mixture was formed. The mixture was either cooled to ambient conditions or kept at 90 C when 9.07 g PG/VG (3:7) solution was added. The blend was then stirred at 90° C. until a visually homogenous formulation solution was achieved with no undissolved chemicals.

Nicotine free base formulation was made by adding 0.5 g nicotine to a beaker followed by adding 9.5 g PG/VG (3:7) solution to the same beaker. The mixture was then stirred at ambient conditions for 10 minutes until a visually homogenous formulation solution was achieved.

Various formulations comprising different nicotine salts can be prepared similarly, or different concentrations of the above-noted nicotine formulations or other nicotine salt formulations can be prepared as one of skill in the art would know to do upon reading the disclosure herein.

Various formulations comprising two or more nicotine salts can be prepared similarly in a solution of 3:7 ratio of propylene glycol (PG)/vegetable glycerin (VG). For example, 0.43 g (2.5% w/w nicotine) of nicotine levulinate salt and 0.34 g (2.5% w/w nicotine) of nicotine acetate salt are added to 9.23 g of PG/VG solution, to achieve a 5% w/w nicotine formulation.

Also provided is another exemplary formulation. For example, 0.23 g (1.33% w/w nicotine) of nicotine benzoate salt (molar ratio 1:1 nicotine/benzoic acid), 0.25 g (1.33% w/w nicotine) of nicotine salicylate salt (molar ratio 1:1 nicotine/salicylic acid) and 0.28 g (1.34% w/w nicotine) of nicotine pyruvate salt (molar ratio 1:2 nicotine/pyruvic acid) are added to 9.25 g of PG/VG solution, to achieve a 5% w/w nicotine formulation.

Example 2

Heart Rate Study of Nicotine Solutions Via e-Cigarette

Exemplary formulations of nicotine levulinate, nicotine benzoate, nicotine succinate, nicotine salicylate, nicotine malate, nicotine pyruvate, nicotine citrate, nicotine freebase, and a control of propylene glycol were prepared as noted in Example 1 in 3% w/w solutions and were administered in the same fashion by an electronic cigarette to the same human subject. About 0.5 mL of each solution was loaded into an "eRoll" cartridge atomizer (joyetech.com) to be used in the study. The atomizer was then attached to an "eRoll" e-cigarette (same manufacturer). The operating temperature was from about 150° C. to about 250° C., or from about 180° C. to about 220° C.

Heart rate measurements were taken for 6 minutes; from 1 minute before start of puffing, for 3 minutes during puffing, and continuing until 2 minutes after end of puffing. The test participant took 10 puffs over 3 minutes in each case. The base heart rate was the average heart rate over the first 1 minute before start of puffing. Heart rate after puffing started was averaged over 20-second intervals. Puffing (inhalation) occurred every 20 seconds for a total of 3 minutes. Normalized heart rate was defined as the ratio between individual heart rate data point and the base heart rate. Final results were presented as normalized heart rate, shown for the first 4 minutes in FIG. 1.

FIG. 1 summarizes results from heart rate measurements taken for a variety of nicotine salt formulations. For ease of reference in reviewing FIG. 1, at the 180-second timepoint, from top to bottom (highest normalized heart rate to lowest normalized heart rate), the nicotine formulations are as follows: nicotine salicylate formulation, nicotine malate formulation, nicotine levulinate formulation (nearly identical to nicotine malate formulation at 180 seconds, thus, as a second reference point: the nicotine malate formulation curve is lower than the nicotine levulinate formulation curve at the 160-second time point), nicotine pyruvate formulation, nicotine benzoate formulation, nicotine citrate formulation, nicotine succinate formulation, and nicotine free base formulation. The bottom curve (lowest normalized heart rate) at the 180-second timepoint is associated with the placebo (100% propylene glycol). The test formulations comprising a nicotine salt cause a faster and more significant rise in heart rate than the placebo. The test formulations comprising a nicotine salt also cause faster and more significant rise when compared with a nicotine freebase formulation with the same amount of nicotine by weight. In addition, the nicotine salts (e.g., nicotine benzoate and nicotine pyruvate) prepared from the acids having calculated vapor pressures between 20-200 mmHg at 200° C. (benzoic acid (171.66 mmHg), with the exception of pyruvic acid (having a boiling point of 165 C), respectively) cause a faster rise in heart rate than the rest. The nicotine salts (e.g., nicotine levulinate, nicotine benzoate, and nicotine salicylate) prepared from the acids (benzoic acid, levulinic acid and salicylic acid, respectively) also cause a more significant heart rate increase. Thus, other suitable nicotine salts formed by the acids with the similar vapor pressure and/or similar boiling point may be used in accordance with the practice of the present invention. This experience of increased heart rate theoretically approaching or theoretically comparable to that of a traditional burned cigarette has not been demonstrated or identified in other electronic cigarette devices. Nor has it been demonstrated or identified in low temperature tobacco vaporization devices (electronic cigarettes) that do not burn the tobacco, even when a nicotine salt was used (a solution of 20% (w/w) or more of nicotine salt) as an additive to the tobacco. Thus the results from this experiment are surprising and unexpected.

Example 3

Satisfaction Study of Nicotine Salt Solution Via e-Cigarette

In addition to the heart rate study shown in Example 2, nicotine formulations (using 3% w/w nicotine formulations as described in Example 1) were used to conduct a satisfaction study in a single test participant. The test participant, an e-cigarette and/or traditional cigarette user, was required to have no nicotine intake for at least 12 hours before the test. The participant took 10 puffs using an e-cigarette (same as used in Example 2) over 3 minutes in each case, and then was asked to rate the level of physical and emotional satisfaction he or she felt on a scale of 0-10, with 0 being no physical or emotional satisfaction. The results indicated that the least satisfying compound was the nicotine free base. Nicotine benzoate, nicotine salicylate, and nicotine succinate all performed well, followed by nicotine pyruvate, nicotine citrate, and nicotine pyruvate.

Based on the Satisfaction Study, the nicotine salts formulations with acids having vapor pressure ranges between >20 mmHg @ 200° C., or 20-200 mmHg @ 200° C., or 100-300 mmHg @ 200° C. provide more satisfaction than the rest (except the pyruvic acid which has boiling point of 165° C.). For reference, it has been determined that salicylic acid has a vapor pressure of about 135.7 mmHg @ 200° C., benzoic acid has a vapor pressure of about 171.7 mmHg @ 200° C., lauric acid has a vapor pressure of about 38 mmHg @ 200° C., and levulinic acid has a vapor pressure of about 149 mmHg @ 200° C.

Example 4

Test Formulation 1 (TF1)

A solution of nicotine levulinate in glycerol comprising nicotine salt used: 1.26 g (12.6% w/w) of 1:3 nicotine levulinate 8.74 g (87.4% w/w) of glycerol—Total weight 10.0 g.

Neat nicotine levulinate was added to the glycerol, and mixed thoroughly. L-Nicotine has a molar mass of 162.2 g, and levulinic acid molar mass is 116.1 g. In a 1:3 molar ratio, the percentage of nicotine in nicotine levulinate by weight is given by: 162.2 g/(162.2 g+(3×116.1 g))=31.8% (w/w).

Example 5

Test Formulation 2 (TF2)

A solution of free base nicotine in glycerol comprising 0.40 g (4.00% w/w) of L-nicotine was dissolved in 9.60 g (96.0% w/w) of glycerol and mixed thoroughly.

Example 6

Heart Rate Study of Nicotine Solutions Via e-Cigarette

Both formulations (TF1 and TF2) were administered in the same fashion by an electronic cigarette to the same human subject: about 0.6 mL of each solution was loaded into "eGo-C" cartridge atomizer (joyetech.com). The atomizer was then attached to an "eVic" e-cigarette (same manufacturer). This model of e-cigarette allows for adjustable voltage, and therefore wattage, through the atomizer. The operating temperature of the e-cigarette is from about 150° C. to about 250° C., or from about 180° C. to about 220° C.

The atomizer in both cases has resistance 2.4 ohms, and the e-cigarette was set to 4.24V, resulting in 7.49 W of power. (P=V^2/R)

Heart rate was measured in a 30-second interval for ten minutes from start of puffing. Test participants took 10 puffs over 3 minutes in each case (solid line ($2^{nd}$ highest peak): cigarette, dark dotted line (highest peak): test formulation 1 (TF1—nicotine salt formulation), light dotted line: test formulation 2 (TF2—nicotine formulation). Comparison between cigarette, TF1, and TF2 is shown in FIG. 2.

Figure 2:
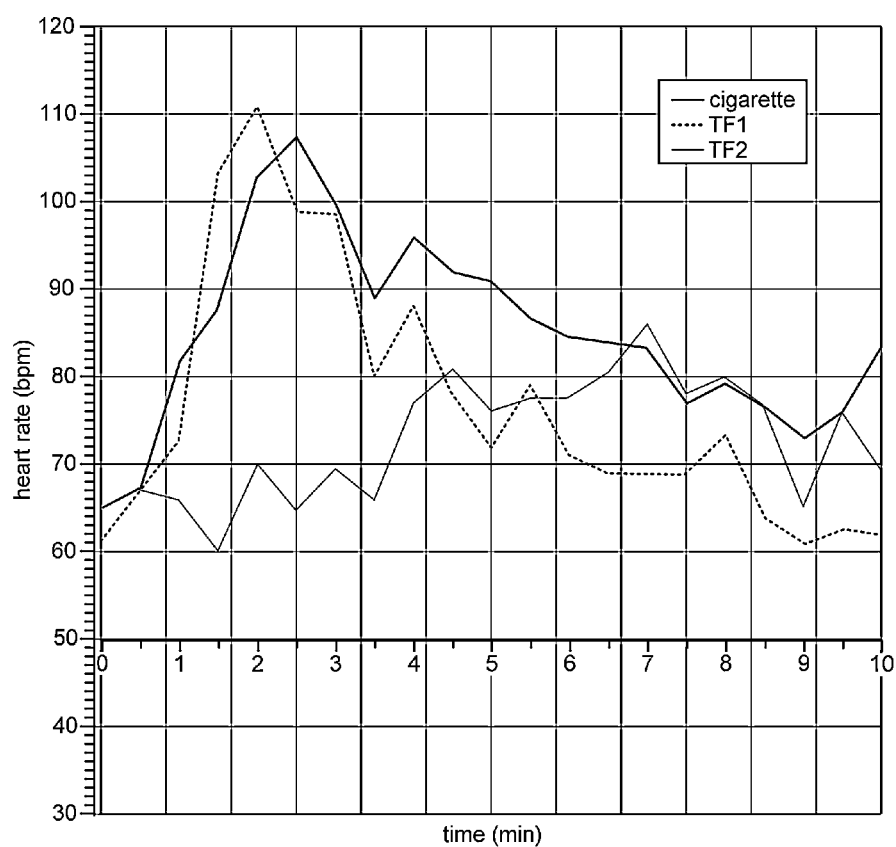
FIG. 2 illustrates results of heart rate data measured for ten minutes from start of puffing. Y-axis is heart rate (bpm) and X-axis represents duration of the test (0 to 10 minutes)

It is clearly shown in FIG. 2 that the test formulation with nicotine levulinate (TF1) causes a faster rise in heart rate than just nicotine (TF2). Also, TF1 more closely resembles the rate of increase for a cigarette. Other salts were tried and also found to increase heart rate relative to a pure nicotine solution. Thus, other suitable nicotine salts that cause the similar effect may be used in accordance with the practice of the present invention. For example, other keto acids (alpha-keto acids, beta-keto acids, gamma-keto acids, and the like) such as pyruvic acid, oxaloacetic acid, acetoacetic acid, and the like. This experience of increased heart rate comparable to that of a traditional burned cigarette has not been demonstrated or identified in other electronic cigarette devices, nor has it been demonstrated or identified in low temperature tobacco vaporization devices that do not burn the tobacco, even when a nicotine salt was used (a solution of 20% (W/W) or more of nicotine salt) as an additive to the tobacco. Thus the results from this experiment are surprising and unexpected.

In addition, the data appears to correlate well with the previous findings shown in FIG. 2.

As previously noted in the Satisfaction Study, the nicotine salts formulations with acids having vapor pressures between 20-300 mmHg @ 200° C. provide more satisfaction than the rest, with the exception of the nicotine salt formulation made with pyruvic acid, which has a boiling point of 165° C., as noted in FIG. 3. Based on the findings herein, it was anticipated that these nicotine salt formulations having either:
  a Vapor Pressure between 20-300 mmHg @ 200° C.,
  a Vapor Pressure >20 mmHg @ 200° C.,
  a difference between boiling point and melting point of at least 50° C., and a boiling point greater than 160° C., and a melting point less than 160° C.,
  a difference between boiling point and melting point of at least 50° C., and a boiling point greater than 160° C., and a melting point less than 160° C.,
  a difference between boiling point and melting point of at least 50° C., and a boiling point at most 40° C. less than operating temperature, and a melting point at least 40° C. lower than operating temperature, or
  a combination thereof produce one or more of the following effects:

$T_{max}$—Time to maximum blood concentration: Based on the results established herein, a user of an e-cigarette comprising the nicotine salt formulation will experience a comparable rate of physical and emotional satisfaction from using a formulation comprising a mixture of nicotine salts prepared with an appropriate acid at least 1.2× to 3× faster than using a formulation comprising a freebase nicotine. As illustrated in FIG. 1: Nicotine from a nicotine salts formulation appears to generate a heartbeat that is nearly 1.2 times that of a normal heart rate for an individual approximately 40 seconds after the commencement of puffing; whereas the nicotine from a nicotine freebase formulation appears to generate a heartbeat that is nearly 1.2 times that of a normal heart rate for an individual approximately 110 seconds after the commencement of puffing; a 2.75× difference in time to achieve a comparable initial satisfaction level.

Again this would not be inconsistent with the data from FIG. 2, where the data illustrated that at approximately 120 seconds (2 minutes), the heart rate of test participants reached a maximum of 105-110 bpm with either a regular cigarette or a nicotine salt formulation (TF1); whereas those same participants heart rates only reached a maximum of approximately 86 bpm at approximately 7 minutes with a nicotine freebase formulation (TF2); also a difference in effect of 1.2 times greater with nicotine salts (and regular cigarettes) versus freebase nicotine.

Further, when considering peak satisfaction levels (achieved at approximately 120 seconds from the initiation of puffing (time=0) and looking at the slope of the line for a normalized heart rate, the approximate slope of those nicotine salt formulations that exceeded the freebase nicotine formulation range between 0.0054 $hr_n$/sec and 0.0025 $hr_n$/sec. By comparison, the slope of the line for the freebase nicotine formulation is about 0.002. This would suggest that the concentration of available nicotine will be delivered to the user at a rate that is between 1.25 and 2.7 times faster than a freebase formulation.

In another measure of performance; $C_{max}$—Maximum blood nicotine concentration; it is anticipated that similar rates of increase will be measured in blood nicotine concentration, as those illustrated above. That is, it was anticipated based on the findings herein, and unexpected based on the art known to date, that there would be comparable $C_{max}$ between the common cigarette and certain nicotine salt formulations, but with a lower $C_{max}$ in a freebase nicotine solution.

Similarly, anticipated based on the findings herein, and unexpected based on the art known to date, that certain nicotine salt formulations would have higher rate of nicotine uptake levels in the blood at early time periods. Indeed, Example 8 presents data for multiple salt formulations consistent with these predictions which were made based on the findings and tests noted herein, and unexpected compared to the art available to date.

Example 7

Heart Rate Study of Nicotine Solutions Via e-Cigarette

Exemplary formulations of nicotine levulinate, nicotine benzoate, nicotine succinate, nicotine salicylate, nicotine malate, nicotine pyruvate, nicotine citrate, nicotine sorbate, nicotine laurate, nicotine freebase, and a control of propylene glycol are prepared as noted in Example 1 and are administered in the same fashion by an electronic cigarette to the same human subject. About 0.5 mL of each solution is loaded into an "eRoll" cartridge atomizer (joyetech.com) to be used in the study. The atomizer is then attached to an "eRoll" e-cigarette (same manufacturer). The operating temperature of the e-cigarette is from about 150° C. to about 250° C., or from about 180° C. to about 220° C.

Heart rate measurements are taken for 6 minutes; from 1 minute before start of puffing, for 3 minutes during puffing, and continuing until 2 minutes after end of puffing. The test participant takes 10 puffs over 3 minutes in each case. The base heart rate is the average heart rate over the first 1 minute before start of puffing. Heart rate after puffing started is averaged over 20-second intervals. Normalized heart rate is defined as the ratio between individual heart rate data point and the base heart rate. Final results are presented as normalized heart rate.

Example 8

Blood Plasma Testing

Blood plasma testing was conducted on three subjects (n=3). Eight test articles were used in this study: one reference cigarette and seven blends used in an e-cigarette device having an operating temperature of the e-cigarette from about 150° C. to about 250° C., or from about 180° C. to about 220° C. The reference cigarette was Pall Mall (New Zealand). Seven blends were tested in the e-cigarette: 2% free base, 2% benzoate, 4% benzoate, 2% citrate, 2% malate, 2% salicylate, and 2% succinate. Except for 2% succinate (n=1), all other blends have n=3. The seven blends were liquid formulations prepared as described in Example 1.

The concentration of nicotine in each of the formulations was confirmed using UV spectrophotometer (Cary 60, manufactured by Agilent). The sample solutions for UV analysis were made by dissolving 20 mg of each of the formulations in 20 mL 0.3% HCl in water. The sample solutions were then scanned in UV spectrophotometer and the characteristic nicotine peak at 259 nm was used to quantify nicotine in the sample against a standard solution of 19.8 μg/mL nicotine in the same diluent. The standard solution was prepared by first dissolving 19.8 mg nicotine in 10 mL 0.3% HCl in water followed by a 1:100 dilution with 0.3% HCl in water. Nicotine concentrations reported for all formulations were within the range of 95%-105% of the claimed concentrations All subjects were able to consume 30-55 mg of the liquid formulation of each tested blend using the e-cigarette.

Literature results: C. Bullen et al, Tobacco Control 2010, 19:98-103 Cigarette (5 min adlib, n=9): $T_{max}$=14.3 (8.8-19.9), $C_{max}$=13.4 (6.5-20.3) 1.4% E-cig (5 min adlib, n=8): $T_{max}$=19.6 (4.9-34.2), $C_{max}$=1.3 (0.0-2.6) Nicorette Inhalator (20 mg/20 min, n=10): $T_{max}$=32.0 (18.7-45.3), $C_{max}$=2.1 (1.0-3.1)

Figure 4:
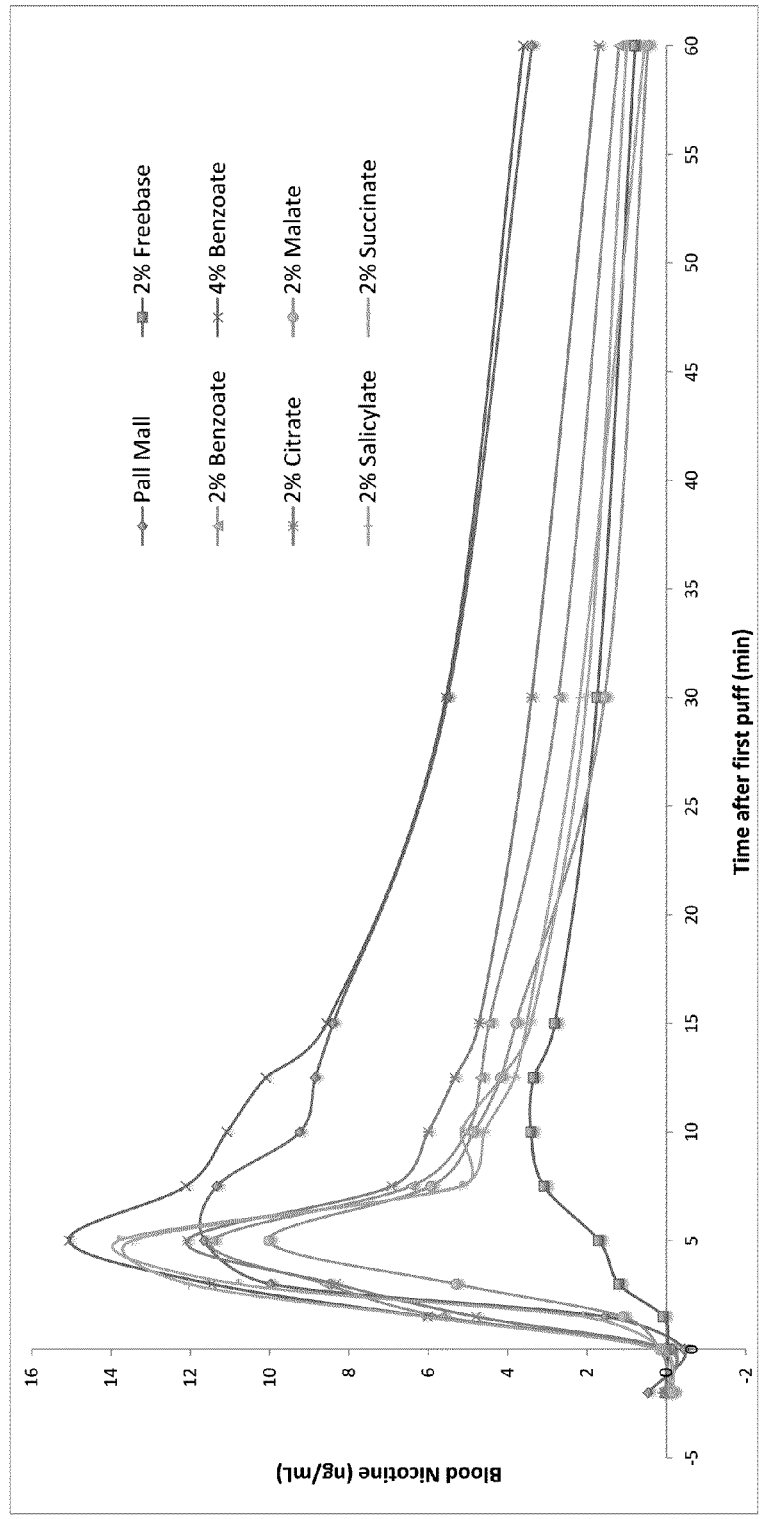
FIG. 4 illustrates the pharmacokinetic profiles for eight test articles in a blood plasma study.

Estimated $C_{max}$ of 2% nicotine blends:

$C_{max}$=Mass consumed*Strength*Bioavailability/(Vol of Distribution*Body Weight)=40 mg*2%*80%/(2.6 L/kg*75 kg)=3.3 ng/mL Estimated $C_{max}$ of 4% nicotine blends:

$C_{max}$=Mass consumed*Strength*Bioavailability/(Vol of Distribution*Body Weight)=40 mg*4%*80%/(2.6 L/kg*75 kg)=6.6 ng/mL Pharmacokinetic profiles of the blood plasma testing are shown in FIG. 4; showing blood nicotine concentrations (ng/mL) over time after the first puff (inhalation) of the aerosol from the e-cigarette or the smoke of the Pall Mall. Ten puffs were taken at 30 sec intervals starting at time=0 and continuing for 4.5 minutes. For ease of reference and review of FIG. 4, at the 5-minute timepoint, the curves on the graph show from top to bottom (highest average blood nicotine concentration to lowest average blood nicotine concentration) are 4% benzoate, 2% succinate, 2% salicylate, 2% citrate, Pall Mall cigarette, 2% benzoate, 2% malate, and 2% free base blend. Although noted as highest to lowest at this time point, this is not to say that there is a statistically significant difference between any of the salt formulations, or between any of the salt formulations and the Pall Mall cigarette. However, it is possible there may be a statistically significant difference between the $C_{max}$ of particular salt formulations, and it is also likely based on the data shown in FIG. 4 and in other studies herein that the freebase formulation is statistically different from salt formulations and/or the Pall Mall with respect to $C_{max}$, since it appears lower than others tested at several time points. One of skill in the art, upon review of the disclosure herein could properly power a test to determine actual statistically-based differences between one or more formulations and the cigarette, or between the formulations themselves in an e-cigarette. For ease of reference Tables 1 & 2 present the amount of nicotine detected (as an average of all users) for each formulation and the Pall Mall, presented in ng/mL, along with $C_{max}$ and $T_{max}$ and AUC. Data from these tables, along with the raw data therefore, was used to generate FIGS. 4, 5, and 6.

TABLE 1

| Time | Pall Mall | 2% Freebase | 2% Benzoate | 4% Benzoate |
|---|---|---|---|---|
| -2 | 0.46 | 0.03 | 0.09 | 0.05 |
| 0 | -0.46 | -0.03 | -0.09 | -0.05 |
| 1.5 | 1.54 | 0.08 | 5.67 | 6.02 |
| 3 | 9.98 | 1.19 | 8.60 | 11.47 |
| 5 | 11.65 | 1.70 | 11.44 | 15.06 |
| 7.5 | 11.34 | 3.09 | 6.43 | 12.12 |
| 10 | 9.24 | 3.42 | 5.03 | 11.08 |
| 12.5 | 8.85 | 3.35 | 4.68 | 10.10 |
| 15 | 8.40 | 2.81 | 4.47 | 8.57 |
| 30 | 5.51 | 1.74 | 2.72 | 5.56 |
| 60 | 3.39 | 0.79 | 1.19 | 3.60 |
| $T_{max}$ (min) | 5.17 | 10.00 | 6.67 | 5.83 |
| $C_{max}$ (ng/mL) | 11.65 | 3.42 | 11.44 | 15.06 |
| AUC (ng * min/mL) | 367.5 | 106.2 | 207.8 | 400.2 |

TABLE 2

| Time | 2% Citrate | 2% Malate | 2% Salicylate | 2% Succinate |
|---|---|---|---|---|
| -2 | 0.06 | -0.17 | -0.19 | -0.06 |
| 0 | -0.06 | 0.17 | 0.19 | 0.06 |
| 1.5 | 4.80 | 1.09 | 6.14 | 2.10 |
| 3 | 8.33 | 5.30 | 12.04 | 10.81 |
| 5 | 12.09 | 10.02 | 13.46 | 13.81 |
| 7.5 | 6.93 | 5.93 | 5.21 | 5.15 |
| 10 | 6.01 | 4.85 | 4.60 | 5.18 |
| 12.5 | 5.34 | 4.17 | 3.83 | 4.17 |
| 15 | 4.72 | 3.79 | 3.52 | 3.41 |
| 30 | 3.40 | 1.56 | 2.19 | 2.01 |
| 60 | 1.70 | 0.46 | 0.55 | 1.00 |
| $T_{max}$ (min) | 5.83 | 5.00 | 4.33 | 5.00 |
| $C_{max}$ (ng/mL) | 12.09 | 10.02 | 13.46 | 13.81 |
| AUC (ng * min/mL) | 238.0 | 146.1 | 182.9 | 179.5 |

Figure 5:
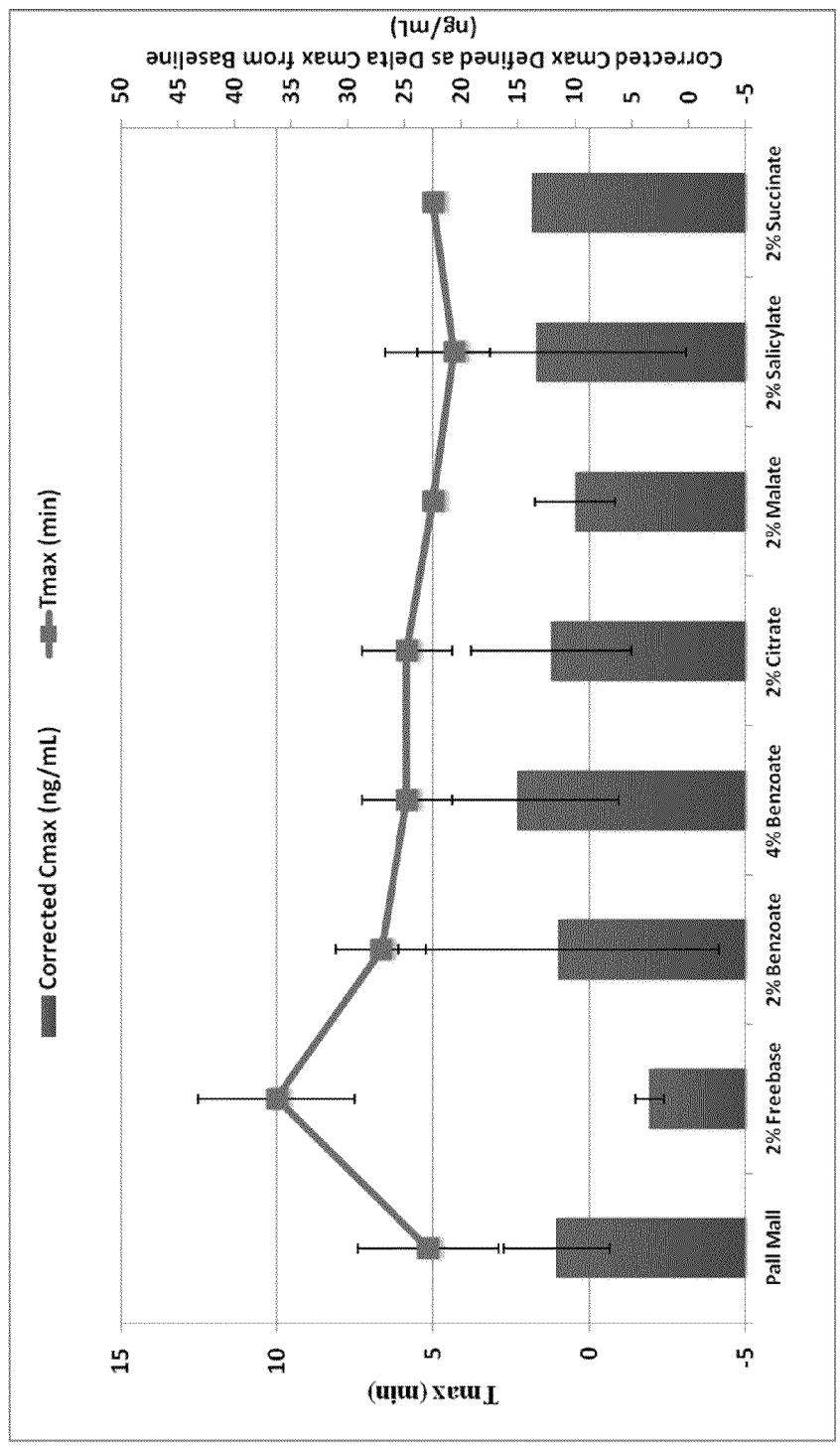
FIG. 5 illustrates the comparison of $C_{max}$ and $T_{max}$ for eight test articles in a blood plasma study.
Figure 6:
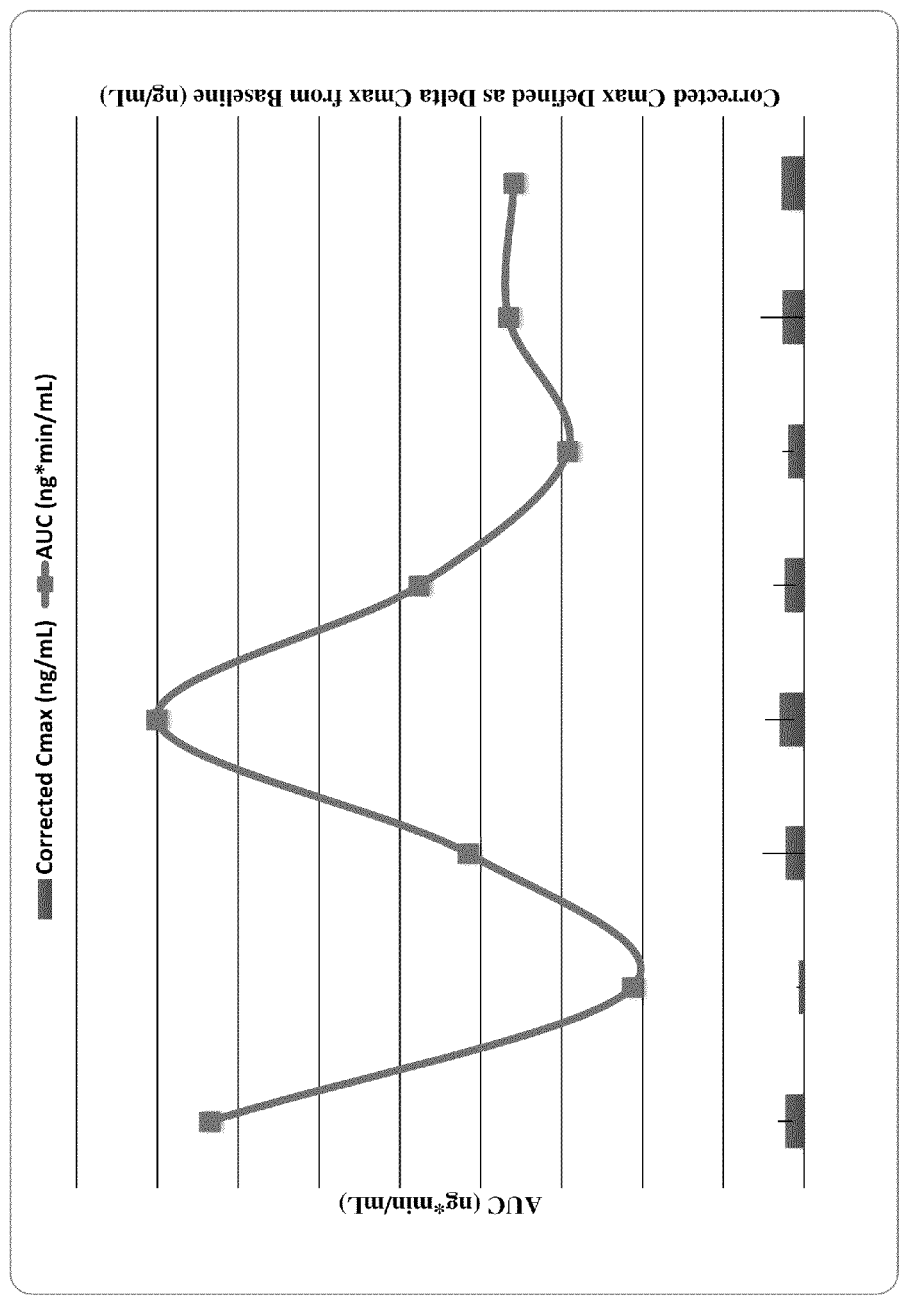
FIG. 6 illustrates the comparison of $C_{max}$ and AUC for eight test articles in a blood plasma study.

Comparison of $T_{max}$ and $C_{max}$ of the seven blends and reference cigarette are shown in FIG. 5. Comparison of $C_{max}$ and AUC of the seven blends and reference cigarette are shown in FIG. 6. Due to the time limit of the wash-period, baseline blood nicotine concentration (at t=−2 and t=0 min) was higher for samples consumed at a later time on the test day. The data in FIGS. 4-6 show corrected blood nicotine concentration values (i.e. apparent blood nicotine concentration at each time point minus baseline nicotine concentration of the same sample).

Rates of nicotine uptake in the blood of the users of each sample within the first 90 seconds are shown in Table 3.

TABLE 3

| Sample | Rate of nicotine uptake (ng/mL/min) |
|---|---|
| 2% Salicylate | 4.09 |
| 2% Benzoate | 3.78 |
| 2% Citrate | 3.20 |
| 2% Succinate | 1.40 |
| Pall Mall (reference) | 1.03 |
| 2% Malate | 0.73 |
| 2% Freebase | 0.05 |
| 4% Benzoate | 4.01 |

Although the $T_{max}$ and $C_{max}$ values are comparable between the tested blends and the reference cigarette (with the exception of the 2% free base blend), the rates of nicotine absorption within the first 90 seconds differed among the test articles. In particular, four blends (2% salicylate, 2% benzoate, 4% benzoate, and 2% citrate) showed markedly higher rates of absorption within the first 90 seconds compared to the other blends and with the reference cigarette. These four blends contain salts (salicylate, benzoate, and citrate) which performed well in the Satisfaction Study of Example 3. Moreover, 2% benzoate and 4% benzoate had comparable rates of absorption, suggesting that a lower concentration of nicotinic salt may not adversely impact the rate of absorption.

Example 9

Blood Plasma Testing

Blood plasma testing is conducted on 24 subjects (n=24). Eight test articles are used in this study: one reference cigarette and seven blends delivered to a user in an e-cigarette as an aerosol. The operating temperature of the e-cigarette is from about 150° C. to about 250° C., or from about 180° C. to about 220° C. The reference cigarette is Pall Mall (New Zealand). Seven blends are tested: 2% free base, 2% benzoate, 4% benzoate, 2% citrate, 2% malate, 2% salicylate, and 2% succinate. The seven blends are liquid formulations prepared according to protocols similar to that described infra and in Example 1.

All subjects are to consume 30-55 mg of the liquid formulation of each tested blend. Ten puffs are to be taken at 30 sec intervals starting at time=0 and continuing for 4.5 minutes. Blood plasma testing is to occur for at least 60 minutes from the first puff (t=0) Pharmacokinetic data (e.g., $C_{max}$, $T_{max}$, AUC) for nicotine in the plasma of users are obtained at various time periods during those 60 minutes, along with rates of nicotine absorption within the first 90 seconds for each test article.

Example 10

Blood Plasma Testing

Blood plasma testing is conducted on twenty-four subjects (n=24). Eleven test articles are used in this study: one reference cigarette and ten blends delivered to a user in an e-cigarette as an aerosol. The reference cigarette is Pall Mall (New Zealand). The operating temperature of the e-cigarette is from about 150° C. to about 250° C., or from about 180° C. to about 220° C. Ten blends are tested: 2% free base, 2% benzoate, 2% sorbate, 2% pyruvate, 2% laurate, 2% levulinate, 2% citrate, 2% malate, 2% salicylate, and 2% succinate. The ten blends are liquid formulations prepared according to protocols similar to that described infra and in Example 1.

All subjects are to consume 30-55 mg of the liquid formulation of each tested blend. Ten puffs are to be taken at 30 sec intervals starting at time=0 and continuing for 4.5 minutes. Blood plasma testing is to occur for at least 60 minutes from the first puff (t=0). Pharmacokinetic data (e.g., $C_{max}$, $T_{max}$, AUC) for nicotine in the plasma of users are obtained at various time periods during those 60 minutes, along with rates of nicotine absorption within the first 90 seconds for each test article.

Example 11

Blood Plasma Testing

Blood plasma testing is conducted on twenty-four subjects (n=24). Twenty-one test articles are used in this study: one reference cigarette and twenty blends delivered to a user in an e-cigarette as an aerosol. The reference cigarette is Pall Mall (New Zealand). The operating temperature of the e-cigarette is from about 150° C. to about 250° C., or from about 180° C. to about 220° C. Twenty blends are tested: 2% free base, 4% free base, 2% benzoate, 4% benzoate, 2% sorbate, 4% sorbate, 2% pyruvate, 4% pyruvate, 2% laurate, 4% laurate, 2% levulinate, 4% levulinate, 2% citrate, 4% citrate, 2% malate, 4% malate, 2% salicylate, 4% salicylate, 2% succinate, and 4% succinate. The twenty blends are liquid formulations prepared according to protocols similar to that described infra and in Example 1.

All subjects are to consume 30-55 mg of the liquid formulation of each tested blend. Ten puffs are to be taken at 30 sec intervals starting at time=0 and continuing for 4.5 minutes. Blood plasma testing is to occur for at least 60 minutes from the first puff (t=0). Pharmacokinetic data (e.g., $C_{max}$, $T_{max}$, AUC) for nicotine in the plasma of users are obtained at various time periods during those 60 minutes, along with rates of nicotine absorption within the first 90 seconds for each test article.

Example 12

Blood Plasma Testing

Blood plasma testing is conducted on twenty-four subjects (n=24). Twenty-one test articles are used in this study: one reference cigarette and twenty blends delivered to a user in an e-cigarette as an aerosol. The reference cigarette is Pall Mall (New Zealand). The operating temperature of the e-cigarette is from about 150° C. to about 250° C., or from about 180° C. to about 220° C. Twenty blends are tested: 2% free base, 1% free base, 2% benzoate, 1% benzoate, 2% sorbate, 1% sorbate, 2% pyruvate, 1% pyruvate, 2% laurate, 1% laurate, 2% levulinate, 1% levulinate, 2% citrate, 1% citrate, 2% malate, 1% malate, 2% salicylate, 1% salicylate, 2% succinate, and 1% succinate. The twenty blends are liquid formulations prepared according to protocols similar to that described infra and in Example 1.

All subjects are to consume 30-55 mg of the liquid formulation of each tested blend. Ten puffs are to be taken at 30 sec intervals starting at time=0 and continuing for 4.5 minutes. Blood plasma testing is to occur for at least 60 minutes from the first puff (t=0). Pharmacokinetic data (e.g., $C_{max}$, $T_{max}$, AUC) for nicotine in the plasma of users are obtained at various time periods during those 60 minutes, along with rates of nicotine absorption within the first 90 seconds for each test article.

Further understanding may be gained through contemplation of the numbered embodiments below.

1. A method of delivering nicotine to a user comprising operating an electronic cigarette to a user wherein the electronic cigarette comprises a nicotine salt formulation comprising a nicotine salt in a biologically acceptable liquid carrier wherein an acid used to form said nicotine salt is characterized by vapor pressure >20 mmHg at 200° C., and inhaling an aerosol generated from the nicotine salt formulation heated by the electronic cigarette.

2. A method of delivering nicotine to a user comprising operating an electronic cigarette to a user wherein the electronic cigarette comprises a nicotine salt formulation comprising a nicotine salt in a biologically acceptable liquid carrier wherein an acid used to form said nicotine salt is characterized by vapor pressure of about 20 to 200 mmHg at 200° C., and inhaling an aerosol generated from the nicotine salt formulation heated by the electronic cigarette.

3. A method of delivering nicotine to a user comprising operating an electronic cigarette wherein the electronic cigarette comprises a nicotine salt formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point, and inhaling an aerosol generated from the nicotine salt formulation heated by the electronic cigarette.

4. A method of delivering nicotine to a user comprising providing an electronic cigarette to a user wherein the electronic cigarette comprises a nicotine salt formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point, and inhaling an aerosol generated from the nicotine salt formulation heated by the electronic cigarette.

5. The method of any one of embodiments 1-3, wherein an operating temperature is from 150° C. to 250° C.

6. The method of any one of embodiments 1-3, wherein an operating temperature is from 180° C. to 220° C.

7. The method any one of embodiments 1-3, wherein an operating temperature is about 200° C.

8. The method of embodiment 4, wherein the operating temperature is from 150° C. to 250° C.

9. The method of embodiment 4, wherein the operating temperature is from 180° C. to 220° C.

10. The method of embodiment 4, wherein the operating temperature is about 200° C.

11. The method any one of embodiments 1-10, wherein the aerosol comprises condensate of the nicotine salt.

12. The method of any one of embodiments 1-10, wherein the aerosol comprises condensate of freebase nicotine.

13. The method of any one of embodiments 1-10, wherein the aerosol comprises condensate of freebase nicotine and condensate of the carrier.

14. The method any one of embodiments 1-10, wherein the aerosol comprises condensate of freebase nicotine and condensate of the acid.

15. The method any one of embodiments 1-14, wherein the aerosol comprises condensate in particle sizes from about 0.1 microns to about 5 microns.

16. The method any one of embodiments 1-14, wherein the aerosol comprises condensate in particle sizes from about 0.1 microns to about 1 or 2 microns.

17. The method any one of embodiments 1-14, wherein the aerosol comprises condensate in particle sizes from about 0.1 microns to about 0.7 microns.

18. The method any one of embodiments 1-14, wherein the aerosol comprises condensate in particle sizes from about 0.3 microns to about 0.4 microns.

19. The method any one of embodiments 1-18, wherein the acid is a carboxylic acid.

20. The method of any one of embodiments 1-18, wherein the acid used to form said nicotine salt is an organic acid.

21. The method of embodiment 20, wherein the organic acid is monocarboxylic acid, aromatic acid, or keto acid.

22. The method of embodiment 20, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

23. The method of any one of embodiments 1-18, wherein the acid used to form the nicotine salt is salicylic acid.

24. The method of any one of embodiments 1-18, wherein the acid used to form the nicotine salt is benzoic acid.

25. The method of any one of embodiments 1-18, wherein the acid used to form the nicotine salt is pyruvic acid.

26. The method of any one of embodiments 1-18, wherein the acid used to form the nicotine salt is sorbic acid.

27. The method of any one of embodiments 1-18, wherein the acid used to form the nicotine salt is lauric acid.

28. The method of any one of embodiments 1-18, wherein the acid used to form the nicotine salt is levulinic acid.

29. The method of any one of embodiments 1-18, wherein said nicotine salt comprises nicotine pyruvate.

30. The method of any one of embodiments 1-18, wherein said nicotine salt comprises nicotine salicylate.

31. The method of any one of embodiments 1-18, wherein said nicotine salt comprises nicotine sorbate.

32. The method of any one of embodiments 1-18, wherein said nicotine salt comprises nicotine laurate.

33. The method of any one of embodiments 1-18, wherein said nicotine salt comprises nicotine levulinate.

34. The method of any one of embodiments 1-18, wherein said nicotine salt comprises nicotine benzoate.

35. The method of any one of embodiments 1-34, wherein the liquid carrier comprises glycerol, propylene glycol, trimethylene glycol, water, ethanol or combinations thereof.

36. The method of any one of embodiments 1-34, wherein the liquid carrier comprises propylene glycol and vegetable glycerin.

37. The method of any one of embodiments 1-34, wherein the liquid carrier comprises 20% to 50% of propylene glycol and 80% to 50% of vegetable glycerin.

38. The method of any one of embodiments 1-34, wherein the liquid carrier comprises 30% propylene glycol and 70% vegetable glycerin.

39. The method of any one of embodiments 1-38, wherein the nicotine salt is in an amount that forms about 0.5% to about 20% nicotine in the inhalable aerosol.

40. The method of any one of embodiments 1-38, wherein the nicotine salt is in an amount that forms about 1% to about 20% nicotine in the inhalable aerosol.

41. The method of any one of embodiments 1-40, wherein the liquid formulation has a nicotine concentration of about 1% (w/w) to about 25% (w/w).

42. The method of any one of embodiments 1-40, wherein the liquid formulation has a nicotine concentration of about 1% (w/w) to about 20% (w/w).

43. The method of any one of embodiments 1-40, wherein the liquid formulation has a nicotine concentration of about 1% (w/w) to about 18% (w/w).

44. The method of any one of embodiments 1-40, wherein the liquid formulation has a nicotine concentration of about 1% (w/w) to about 15% (w/w).

45. The method of any one of embodiments 1-40, wherein the liquid formulation has a nicotine concentration of about 4% (w/w) to about 12% (w/w).

46. The method of any one of embodiments 1-40, wherein the liquid formulation has a nicotine concentration of about 4% (w/w).

47. The method of any one of embodiments 1-40, wherein the liquid formulation has a nicotine concentration of about 2% (w/w).

48. The method of any one of embodiments 1-47, wherein the formulation further comprises a flavorant.

49. The method of any one of embodiments 1-48, wherein the formulation is non-corrosive to an electronic cigarette.

50. The method of any one of embodiments 1-49, wherein the acid is stable at and below operating temperature or about 200° C.

51. The method of any one of embodiments 1-50, wherein the acid does not decompose at and below operating temperature or about 200° C.

52. The method of any one of embodiments 1-51, wherein the acid does not oxidize at and below operating temperature or about 200° C.

53. The method of any one of embodiments 1-52, wherein the formulation is non-corrosive to the electronic cigarette.

54. The method of any one of embodiments 1-53, wherein the formulation is non-toxic to a user of the electronic cigarette.

55. The method of any one of embodiments 1-54, wherein the formulation further comprises one or more additional nicotine salts in a biologically acceptable liquid carrier suitable for generating the inhalable aerosol upon heating.

56. The method of embodiment 55, wherein a second acid used to form the additional nicotine salt is selected from the group consisting of salicylic acid, sorbic acid, benzoic acid, pyruvic acid, lauric acid, and levulinic acid.

57. A method of delivering nicotine to the blood of a user, said method comprising providing an aerosol that is inhaled by the user from an electronic cigarette that comprises a nicotine salt formulation wherein providing the aerosol comprises the electronic cigarette heating the formulation thereby generating the aerosol, wherein the aerosol is effective in delivering a level of nicotine in the blood of the user that is at least 5 ng/mL at about 1.5 minutes after a first puff of ten puffs of the aerosol, each puff taken at 30 second intervals.

58. The method of embodiment 54, wherein the nicotine salt formulation comprises a nicotine salt in a biologically acceptable liquid carrier wherein an acid used to form said nicotine salt is characterized by vapor pressure >20 mmHg at 200° C.

59. The method of embodiment 54, wherein the nicotine salt formulation comprises a nicotine salt in a biologically acceptable liquid carrier wherein an acid used to form said nicotine salt is characterized by vapor pressure of about 20 to 200 mmHg at 200° C.

60. The method of embodiment 54, wherein the nicotine salt formulation comprises a nicotine salt in a biologically acceptable liquid carrier wherein an acid used to form said nicotine salt is further characterized by a melting point <160° C., a boiling point >160° C., and at least a 50-degree difference between the melting point and the boiling point.

61. The method of any one of embodiments 57-60, wherein the heating of the formulation is at a temperature from 150° C. to 250° C.

62. The method of any one of embodiments 57-60, wherein the heating of the formulation is at a temperature from 180° C. to 220° C.

63. The method of any one of embodiments 57-60, wherein the heating of the formulation is at a temperature of about 200° C.

64. The method of embodiment 54, wherein the nicotine salt formulation comprises a nicotine salt in a biologically acceptable liquid carrier wherein an acid used to form said nicotine salt is further characterized by a melting point at least 40 degrees lower than the operating temperature of the electronic cigarette, a boiling point no more than 40 degrees lower than the operating temperature of the electronic cigarette, and at least a 50-degree difference between the melting point and the boiling point; and the operating temperature is 200° C.

65. The method of any one of embodiments 57-64, wherein the Cmax is over 10 ng/mL on average.

66. The method of any one of embodiments 57-64, wherein the Cmax is over 11 ng/mL on average.

67. The method of any one of embodiments 57-64, wherein the Cmax is between 10 ng/mL and 16 ng/mL on average.

68. The method of any one of embodiments 57-64, wherein the Cmax is between 11 ng/mL and 15 ng/mL on average.

69. The method of any one of embodiments 57-64, wherein the Cmax is between 11 ng/mL and 14 ng/mL on average.

70. The method of any one of embodiments 57-69, wherein the Tmax under 10 minutes on average.

71. The method of any one of embodiments 57-69, wherein the Tmax is under 9 minutes on average.

72. The method of any one of embodiments 57-69, wherein the Tmax is under 8 minutes on average.

73. The method of any one of embodiments 57-69, wherein the Tmax is under 7 minutes on average.

74. The method of any one of embodiments 54-63, wherein the Tmax is from 3 minutes to 10 minutes on average.

75. The method of any one of embodiments 57-69, wherein the Tmax is from 3 minutes to 7.5 minutes on average.

76. The method of any one of embodiments 57-75, wherein the aerosol comprises condensate of the nicotine salt.

77. The method of any one of embodiments 57-75, wherein the aerosol comprises condensate of freebase nicotine.

78. The method of any one of embodiments 57-75, wherein the aerosol comprises condensate of freebase nicotine and condensate of the carrier.

79. The method of any one of embodiments 57-75, wherein the aerosol comprises condensate of freebase nicotine and condensate of the acid.

80. The method of any one of embodiments 57-79, wherein the aerosol comprises condensate in particle sizes from about 0.1 microns to about 5 microns.

81. The method of any one of embodiments 57-79, wherein the aerosol comprises condensate in particle sizes from about 0.1 microns to about 1 or 2 microns.

82. The method of any one of embodiments 57-79, wherein the aerosol comprises condensate in particle sizes from about 0.1 microns to about 0.7 microns.

83. The method of any one of embodiments 57-79, wherein the aerosol comprises condensate in particle sizes from about 0.3 microns to about 0.4 microns.

84. The method of any one of embodiments 57-83, wherein the acid is a carboxylic acid.

85. The method of any one of embodiments 57-83, wherein the acid used to form said nicotine salt is an organic acid.

86. The method of embodiment 85, wherein the organic acid is monocarboxylic acid, aromatic acid, or keto acid.

87. The method of embodiment 85, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

88. The method of any one of embodiments 57-83, wherein the acid used to form the nicotine salt is salicylic acid.

89. The method of any one of embodiments 57-83, wherein the acid used to form the nicotine salt is benzoic acid.

90. The method of any one of embodiments 57-83, wherein the acid used to form the nicotine salt is pyruvic acid.

91. The method of any one of embodiments 57-83, wherein the acid used to form the nicotine salt is sorbic acid.

92. The method of any one of embodiments 57-83, wherein the acid used to form the nicotine salt is lauric acid.

93. The method of any one of embodiments 57-83, wherein the acid used to form the nicotine salt is levulinic acid.

94. The method of any one of embodiments 57-83, wherein said nicotine salt comprises nicotine pyruvate.

95. The method of any one of embodiments 57-83, wherein said nicotine salt comprises nicotine salicylate.

96. The method of any one of embodiments 57-83, wherein said nicotine salt comprises nicotine sorbate.

97. The method of any one of embodiments 57-83, wherein said nicotine salt comprises nicotine laurate.

98. The method of any one of embodiments 57-83, wherein said nicotine salt comprises nicotine levulinate.

99. The method of any one of embodiments 57-83, wherein said nicotine salt comprises nicotine benzoate.

100. The method of any one of embodiments 57-99, wherein the liquid carrier comprises glycerol, propylene glycol, trimethylene glycol, water, ethanol or combinations thereof.

101. The method of any one of embodiments 57-99, wherein the liquid carrier comprises propylene glycol and vegetable glycerin.

102. The method of any one of embodiments 57-99, wherein the liquid carrier comprises 20% to 50% of propylene glycol and 80% to 50% of vegetable glycerin.

103. The method of any one of embodiments 57-99, wherein the liquid carrier comprises 30% propylene glycol and 70% vegetable glycerin.

104. The method of any one of embodiments 57-103, wherein the nicotine salt is in an amount that forms about 0.5% to about 20% nicotine in the inhalable aerosol.

105. The method of any one of embodiments 57-103, wherein the nicotine salt is in an amount that forms about 1% to about 20% nicotine in the inhalable aerosol.

106. The method of any one of embodiments 57-105, wherein the liquid formulation has a nicotine concentration of about 1% (w/w) to about 25% (w/w).

107. The method of any one of embodiments 57-105, wherein the liquid formulation has a nicotine concentration of about 1% (w/w) to about 20% (w/w).

108. The method of any one of embodiments 57-105, wherein the liquid formulation has a nicotine concentration of about 1% (w/w) to about 18% (w/w).

109. The method of any one of embodiments 57-105, wherein the liquid formulation has a nicotine concentration of about 1% (w/w) to about 15% (w/w).

110. The method of any one of embodiments 57-105, wherein the liquid formulation has a nicotine concentration of about 4% (w/w) to about 12% (w/w).

111. The method of any one of embodiments 57-105, wherein the liquid formulation has a nicotine concentration of about 4% (w/w).

112. The method of any one of embodiments 57-105, wherein the liquid formulation has a nicotine concentration of about 2% (w/w).

113. The method of any one of embodiments 57-112, wherein the formulation further comprises a flavorant.

114. The method of any one of embodiments 57-113, wherein the formulation is non-corrosive to an electronic cigarette.

115. The method of any one of embodiments 57-114, wherein the acid is stable at and below operating temperature or about 200° C.

116. The method of any one of embodiments 57-115, wherein the acid does not decompose at and below operating temperature or about 200° C.

117. The method of any one of embodiments 57-116, wherein the acid does not oxidize at and below operating temperature or about 200° C.

118. The method of any one of embodiments 57-117, wherein the formulation is non-corrosive to the electronic cigarette.

119. The method of any one of embodiments 57-118, wherein the formulation is non-toxic to a user of the electronic cigarette.

120. The method of any one of embodiments 57-119, wherein the formulation further comprises one or more additional nicotine salts in a biologically acceptable liquid carrier suitable for generating the inhalable aerosol upon heating.

121. The method of embodiment 120, wherein a second acid used to form the additional nicotine salt is selected from the group consisting of salicylic acid, sorbic acid, benzoic acid, pyruvic acid, lauric acid, and levulinic acid.

122. A nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is characterized by vapor pressure >20 mmHg at 200° C.

123. A nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is characterized by vapor pressure of about 20 to 200 mmHg at 200° C.

124. A nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

125. A nicotine salt liquid formulation in an electronic cigarette for generating an inhalable aerosol upon heating in the electronic cigarette, the formulation in the cigarette comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

126. The nicotine salt liquid formulation in the electronic cigarette of any one of embodiments 122-124, wherein the electronic cigarette heats the nicotine salt formulation to an operating temperature from 150° C. to 250° C.

127. The nicotine salt liquid formulation in the electronic cigarette of any one of embodiments 122-124, wherein the electronic cigarette heats the nicotine salt formulation to an operating temperature from 180° C. to 220° C.

128. The nicotine salt liquid formulation in the electronic cigarette of any one of embodiments 122-124, wherein the electronic cigarette heats the nicotine salt formulation to an operating temperature of about 200° C.

129. The nicotine salt liquid formulation in the electronic cigarette of embodiment 125, wherein the operating temperature is from 150° C. to 250° C.

130. The nicotine salt liquid formulation in the electronic cigarette of embodiment 125, wherein the operating temperature is from 180° C. to 220° C.

131. The nicotine salt liquid formulation in the electronic cigarette of embodiment 125, wherein the operating temperature is about 200° C.

132. The nicotine salt liquid formulation in the electronic cigarette of any one of embodiments 122-131, wherein the acid is a carboxylic acid.

133. The nicotine salt liquid formulation in the electronic cigarette of any one of embodiments 122-131, wherein the acid used to form said nicotine salt is an organic acid.

134. The nicotine salt liquid formulation in the electronic cigarette of embodiment 133, wherein the organic acid is monocarboxylic acid, aromatic acid, or keto acid.

135. The nicotine salt liquid formulation in the electronic cigarette of embodiment 133, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

136. The nicotine salt liquid formulation in the electronic cigarette of any one of embodiments 122-131, wherein the acid used to form the nicotine salt is salicylic acid.

137. The nicotine salt liquid formulation in the electronic cigarette of any one of embodiments 122-131, wherein the acid used to form the nicotine salt is benzoic acid.

138. The nicotine salt liquid formulation in the electronic cigarette of any one of embodiments 122-131, wherein the acid used to form the nicotine salt is pyruvic acid.

139. The nicotine salt liquid formulation in the electronic cigarette of any one of embodiments 122-131, wherein the acid used to form the nicotine salt is sorbic acid.

140. The nicotine salt liquid formulation in the electronic cigarette of any one of embodiments 122-131, wherein the acid used to form the nicotine salt is lauric acid.

141. The nicotine salt liquid formulation in the electronic cigarette of any one of embodiments 122-131, wherein the acid used to form the nicotine salt is levulinic acid.

142. The nicotine salt liquid formulation in the electronic cigarette of any one of embodiments 122-131, wherein said nicotine salt comprises nicotine pyruvate.

143. The nicotine salt liquid formulation in the electronic cigarette of any one of embodiments 122-131, wherein said nicotine salt comprises nicotine salicylate.

144. The nicotine salt liquid formulation in the electronic cigarette of any one of embodiments 122-131, wherein said nicotine salt comprises nicotine sorbate.

145. The nicotine salt liquid formulation in the electronic cigarette of any one of embodiments 122-131, wherein said nicotine salt comprises nicotine laurate.

146. The nicotine salt liquid formulation in the electronic cigarette of any one of embodiments 122-131, wherein said nicotine salt comprises nicotine levulinate.

147. The nicotine salt liquid formulation in the electronic cigarette of any one of embodiments 122-131, wherein said nicotine salt comprises nicotine benzoate.

148. The nicotine salt liquid formulation in the electronic cigarette of any one of embodiments 122-147, wherein the liquid carrier comprises glycerol, propylene glycol, trimethylene glycol, water, ethanol or combinations thereof.

149. The nicotine salt liquid formulation in the electronic cigarette of any one of embodiments 122-147, wherein the liquid carrier comprises propylene glycol and vegetable glycerin.

150. The nicotine salt liquid formulation in the electronic cigarette of any one of embodiments 122-147, wherein the liquid carrier comprises 20% to 50% of propylene glycol and 80% to 50% of vegetable glycerin.

151. The nicotine salt liquid formulation in the electronic cigarette of any one of embodiments 122-147, wherein the liquid carrier comprises 30% propylene glycol and 70% vegetable glycerin.

152. The nicotine salt liquid formulation in the electronic cigarette of any one of embodiments 122-151, wherein the nicotine salt is in an amount that forms about 0.5% to about 20% nicotine in the inhalable aerosol.

153. The nicotine salt liquid formulation in the electronic cigarette of any one of embodiments 122-151, wherein the nicotine salt is in an amount that forms about 1% to about 20% nicotine in the inhalable aerosol.

154. The nicotine salt liquid formulation in the electronic cigarette of any one of embodiments 122-153, wherein the liquid formulation has a nicotine concentration of about 1% (w/w) to about 25% (w/w).

155. The nicotine salt liquid formulation in the electronic cigarette of any one of embodiments 122-153, wherein the liquid formulation has a nicotine concentration of about 1% (w/w) to about 20% (w/w).

156. The nicotine salt liquid formulation in the electronic cigarette of any one of embodiments 122-153, wherein the liquid formulation has a nicotine concentration of about 1% (w/w) to about 18% (w/w).

157. The nicotine salt liquid formulation in the electronic cigarette of any one of embodiments 122-153, wherein the liquid formulation has a nicotine concentration of about 1% (w/w) to about 15% (w/w).

158. The nicotine salt liquid formulation in the electronic cigarette of any one of embodiments 122-153, wherein the liquid formulation has a nicotine concentration of about 4% (w/w) to about 12% (w/w).

159. The nicotine salt liquid formulation in the electronic cigarette of any one of embodiments 122-153, wherein the liquid formulation has a nicotine concentration of about 4% (w/w).

160. The nicotine salt liquid formulation in the electronic cigarette of any one of embodiments 122-153, wherein the liquid formulation has a nicotine concentration of about 2% (w/w).

161. The nicotine salt liquid formulation in the electronic cigarette of any one of embodiments 122-160, wherein the formulation further comprises a flavorant.

162. The nicotine salt liquid formulation in the electronic cigarette of any one of embodiments 122-161, wherein the formulation is non-corrosive to an electronic cigarette.

163. The nicotine salt liquid formulation in the electronic cigarette of any one of embodiments 122-162, wherein the acid is stable at and below operating temperature or about 200° C.

164. The nicotine salt liquid formulation in the electronic cigarette of any one of embodiments 122-163, wherein the acid does not decompose at and below operating temperature or about 200° C.

165. The nicotine salt liquid formulation in the electronic cigarette of any one of embodiments 122-164, wherein the acid does not oxidize at and below operating temperature or about 200° C.

166. The nicotine salt liquid formulation in the electronic cigarette of any one of embodiments 122-165, wherein the formulation is non-corrosive to the electronic cigarette.

167. The nicotine salt liquid formulation in the electronic cigarette of any one of embodiments 122-166, wherein the formulation is non-toxic to a user of the electronic cigarette.

168. The nicotine salt liquid formulation in the electronic cigarette of any one of embodiments 122-167 further comprising one or more additional nicotine salts in a biologically acceptable liquid carrier suitable for generating the inhalable aerosol upon heating.

169. The nicotine salt liquid formulation in the electronic cigarette of embodiment 168, wherein a second acid used to form the additional nicotine salt is selected from the group consisting of salicylic acid, sorbic acid, benzoic acid, pyruvic acid, lauric acid, and levulinic acid.

170. A nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is characterized by vapor pressure >20 mmHg at 200° C.

171. A nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is characterized by vapor pressure of about 20 to 200 mmHg at 200° C.

172. A nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

173. A nicotine salt liquid formulation for generating an inhalable aerosol upon heating in the electronic cigarette, the nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

174. The nicotine salt liquid formulation of any one of embodiments 170-172, wherein the electronic cigarette heats the nicotine salt formulation to an operating temperature from 150° C. to 250° C.

175. The nicotine salt liquid formulation of any one of embodiments 170-172, wherein the electronic cigarette heats the nicotine salt formulation to an operating temperature from 180° C. to 220° C.

176. The nicotine salt liquid formulation of any one of embodiments 170-172, wherein the electronic cigarette heats the nicotine salt formulation to an operating temperature of about 200° C.

177. The nicotine salt liquid formulation of embodiment 173, wherein the operating temperature is from 150° C. to 250° C.

178. The nicotine salt liquid formulation of embodiment 173, wherein the operating temperature is from 180° C. to 220° C.

179. The nicotine salt liquid formulation of embodiment 173, wherein the operating temperature is about 200° C.

180. The nicotine salt liquid formulation of any one of embodiments 170-179, wherein the acid is a carboxylic acid.

181. The nicotine salt liquid formulation of any one of embodiments 170-179, wherein the acid used to form said nicotine salt is an organic acid.

182. The nicotine salt liquid formulation of embodiment 181, wherein the organic acid is monocarboxylic acid, aromatic acid, or keto acid.

183. The nicotine salt liquid formulation of embodiment 181, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

184. The liquid formulation of any one of embodiments 170-179, wherein the acid used to form the nicotine salt is salicylic acid.

185. The nicotine salt liquid formulation of any one of embodiments 170-179, wherein the acid used to form the nicotine salt is benzoic acid.

186. The nicotine salt liquid formulation of any one of embodiments 170-179, wherein the acid used to form the nicotine salt is pyruvic acid.

187. The nicotine salt liquid formulation of any one of embodiments 170-179, wherein the acid used to form the nicotine salt is sorbic acid.

188. The nicotine salt liquid formulation of any one of embodiments 170-179, wherein the acid used to form the nicotine salt is lauric acid.

189. The nicotine salt liquid formulation of any one of embodiments 170-179, wherein the acid used to form the nicotine salt is levulinic acid.

190. The nicotine salt liquid formulation of any one of embodiments 170-179, wherein said nicotine salt comprises nicotine pyruvate.

191. The nicotine salt liquid formulation of any one of embodiments 170-179, wherein said nicotine salt comprises nicotine salicylate.

192. The nicotine salt liquid formulation of any one of embodiments 170-179, wherein said nicotine salt comprises nicotine sorbate.

193. The nicotine salt liquid formulation of any one of embodiments 170-179, wherein said nicotine salt comprises nicotine laurate.

194. The nicotine salt liquid formulation of any one of embodiments 170-179, wherein said nicotine salt comprises nicotine levulinate.

195. The nicotine salt liquid formulation of any one of embodiments 170-179, wherein said nicotine salt comprises nicotine benzoate.

196. The nicotine salt liquid formulation of any one of embodiments 170-195, wherein the liquid carrier comprises glycerol, propylene glycol, trimethylene glycol, water, ethanol or combinations thereof.

197. The nicotine salt liquid formulation of any one of embodiments 170-195, wherein the liquid carrier comprises propylene glycol and vegetable glycerin.

198. The nicotine salt liquid formulation of any one of embodiments 170-195, wherein the liquid carrier comprises 20% to 50% of propylene glycol and 80% to 50% of vegetable glycerin.

199. The nicotine salt liquid formulation of any one of embodiments 170-195, wherein the liquid carrier comprises 30% propylene glycol and 70% vegetable glycerin.

200. The nicotine salt liquid formulation of any one of embodiments 170-199, wherein the nicotine salt is in an amount that forms about 0.5% to about 20% nicotine in the inhalable aerosol.

201. The nicotine salt liquid formulation of any one of embodiments 170-199, wherein the nicotine salt is in an amount that forms about 1% to about 20% nicotine in the inhalable aerosol.

202. The nicotine salt liquid formulation of any one of embodiments 170-201, wherein the liquid formulation has a nicotine concentration of about 1% (w/w) to about 25% (w/w).

203. The nicotine salt liquid formulation of any one of embodiments 170-201, wherein the liquid formulation has a nicotine concentration of about 1% (w/w) to about 20% (w/w).

204. The nicotine salt liquid formulation of any one of embodiments 170-201, wherein the liquid formulation has a nicotine concentration of about 1% (w/w) to about 18% (w/w).

205. The nicotine salt liquid formulation of any one of embodiments 170-201, wherein the liquid formulation has a nicotine concentration of about 1% (w/w) to about 15% (w/w).

206. The nicotine salt liquid formulation of any one of embodiments 170-201, wherein the liquid formulation has a nicotine concentration of about 4% (w/w) to about 12% (w/w).

207. The nicotine salt liquid formulation of any one of embodiments 170-201, wherein the liquid formulation has a nicotine concentration of about 4% (w/w).

208. The nicotine salt liquid formulation of any one of embodiments 170-201, wherein the liquid formulation has a nicotine concentration of about 2% (w/w).

209. The nicotine salt liquid formulation of any one of embodiments 170-208, wherein the formulation further comprises a flavorant.

210. The nicotine salt liquid formulation of any one of embodiments 170-209, wherein the formulation is non-corrosive to an electronic cigarette.

211. The nicotine salt liquid formulation of any one of embodiments 170-210, wherein the acid is stable at and below operating temperature or about 200° C.

212. The nicotine salt liquid formulation of any one of embodiments 170-211, wherein the acid does not decompose at and below operating temperature or about 200° C.

213. The nicotine salt liquid formulation of any one of embodiments 170-212, wherein the acid does not oxidize at and below operating temperature or about 200° C.

214. The nicotine salt liquid formulation of any one of embodiments 170-213, wherein the formulation is non-corrosive to the electronic cigarette.

215. The nicotine salt liquid formulation of any one of embodiments 170-214, wherein the formulation is non-toxic to a user of the electronic cigarette.

216. The nicotine salt liquid formulation of any one of embodiments 170-215, further comprising one or more additional nicotine salts in a biologically acceptable liquid carrier suitable for generating the inhalable aerosol upon heating.

217. The nicotine salt liquid formulation of embodiment 216, wherein a second acid used to form the additional nicotine salt is selected from the group consisting of salicylic acid, sorbic acid, benzoic acid, pyruvic acid, lauric acid, and levulinic acid.

218. A nicotine salt liquid formulation for use in an electronic cigarette the nicotine salt liquid formulation comprising a nicotine salt in a biologically acceptable liquid carrier wherein an acid used to form said nicotine salt is characterized by vapor pressure >20 mmHg at 200° C.

219. A nicotine salt liquid formulation for use in an electronic cigarette the nicotine salt liquid formulation comprising a nicotine salt in a biologically acceptable liquid carrier wherein an acid used to form said nicotine salt is characterized by vapor pressure of about 20 to 200 mmHg at 200° C.

220. A nicotine salt liquid formulation for use in an electronic cigarette the nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

221. A nicotine salt liquid formulation for use in an electronic cigarette the nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

222. The nicotine salt liquid formulation of any one of embodiments 218-220, wherein the electronic cigarette heats the nicotine salt formulation to an operating temperature from 150° C. to 250° C.

223. The nicotine salt liquid formulation of any one of embodiments 218-220, wherein the electronic cigarette heats the nicotine salt formulation to an operating temperature from 180° C. to 220° C.

224. The nicotine salt liquid formulation of any one of embodiments 218-220, wherein the electronic cigarette heats the nicotine salt formulation to an operating temperature of about 200° C.

225. The nicotine salt liquid formulation of embodiment 221, wherein the operating temperature is from 150° C. to 250° C.

226. The nicotine salt liquid formulation of embodiment 221, wherein the operating temperature is from 180° C. to 220° C.

227. The nicotine salt liquid formulation of embodiment 221, wherein the operating temperature is about 200° C.

228. The nicotine salt liquid formulation of any one of embodiments 218-227, wherein the acid is a carboxylic acid.

229. The nicotine salt liquid formulation of any one of embodiments 218-227, wherein the acid used to form said nicotine salt is an organic acid.

230. The nicotine salt liquid formulation of embodiment 229, wherein the organic acid is monocarboxylic acid, aromatic acid, or keto acid.

231. The nicotine salt liquid formulation of embodiment 229, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

232. The liquid formulation of any one of embodiments 218-227, wherein the acid used to form the nicotine salt is salicylic acid.

233. The nicotine salt liquid formulation of any one of embodiments 218-227, wherein the acid used to form the nicotine salt is benzoic acid.

234. The nicotine salt liquid formulation of any one of embodiments 218-227, wherein the acid used to form the nicotine salt is pyruvic acid.

235. The nicotine salt liquid formulation of any one of embodiments 218-227, wherein the acid used to form the nicotine salt is sorbic acid.

236. The nicotine salt liquid formulation of any one of embodiments 218-227, wherein the acid used to form the nicotine salt is lauric acid.

237. The nicotine salt liquid formulation of any one of embodiments 218-227, wherein the acid used to form the nicotine salt is levulinic acid.

238. The nicotine salt liquid formulation of any one of embodiments 218-227, wherein said nicotine salt comprises nicotine pyruvate.

239. The nicotine salt liquid formulation of any one of embodiments 218-227, wherein said nicotine salt comprises nicotine salicylate.

240. The nicotine salt liquid formulation of any one of embodiments 218-227, wherein said nicotine salt comprises nicotine sorbate.

241. The nicotine salt liquid formulation of any one of embodiments 218-227, wherein said nicotine salt comprises nicotine laurate.

242. The nicotine salt liquid formulation of any one of embodiments 218-227, wherein said nicotine salt comprises nicotine levulinate.

243. The nicotine salt liquid formulation of any one of embodiments 218-227, wherein said nicotine salt comprises nicotine benzoate.

244. The nicotine salt liquid formulation of any one of embodiments 218-243, wherein the liquid carrier comprises glycerol, propylene glycol, trimethylene glycol, water, ethanol or combinations thereof.

245. The nicotine salt liquid formulation of any one of embodiments 218-243, wherein the liquid carrier comprises propylene glycol and vegetable glycerin.

246. The nicotine salt liquid formulation of any one of embodiments 218-243, wherein the liquid carrier comprises 20% to 50% of propylene glycol and 80% to 50% of vegetable glycerin.

247. The nicotine salt liquid formulation of any one of embodiments 218-243, wherein the liquid carrier comprises 30% propylene glycol and 70% vegetable glycerin.

248. The nicotine salt liquid formulation of any one of embodiments 218-247, wherein the nicotine salt is in an amount that forms about 0.5% to about 20% nicotine in the inhalable aerosol.

249. The nicotine salt liquid formulation of any one of embodiments 218-247, wherein the nicotine salt is in an amount that forms about 1% to about 20% nicotine in the inhalable aerosol.

250. The nicotine salt liquid formulation of any one of embodiments 218-247, wherein the liquid formulation has a nicotine concentration of about 1% (w/w) to about 25% (w/w).

251. The nicotine salt liquid formulation of any one of embodiments 218-247, wherein the liquid formulation has a nicotine concentration of about 1% (w/w) to about 20% (w/w).

252. The nicotine salt liquid formulation of any one of embodiments 218-247, wherein the liquid formulation has a nicotine concentration of about 1% (w/w) to about 18% (w/w).

253. The nicotine salt liquid formulation of any one of embodiments 218-247, wherein the liquid formulation has a nicotine concentration of about 1% (w/w) to about 15% (w/w).

254. The nicotine salt liquid formulation of any one of embodiments 218-247, wherein the liquid formulation has a nicotine concentration of about 4% (w/w) to about 12% (w/w).

255. The nicotine salt liquid formulation of any one of embodiments 218-247, wherein the liquid formulation has a nicotine concentration of about 4% (w/w).

256. The nicotine salt liquid formulation of any one of embodiments 218-247, wherein the liquid formulation has a nicotine concentration of about 2% (w/w).

257. The nicotine salt liquid formulation of any one of embodiments 218-256, wherein the formulation further comprises a flavorant.

258. The nicotine salt liquid formulation of any one of embodiments 218-257, wherein the formulation is non-corrosive to an electronic cigarette.

259. The nicotine salt liquid formulation of any one of embodiments 218-258, wherein the acid is stable at and below operating temperature or about 200° C.

260. The nicotine salt liquid formulation of any one of embodiments 218-259, wherein the acid does not decompose at and below operating temperature or about 200° C.

261. The nicotine salt liquid formulation of any one of embodiments 218-260, wherein the acid does not oxidize at and below operating temperature or about 200° C.

262. The nicotine salt liquid formulation of any one of embodiments 218-261, wherein the formulation is non-corrosive to the electronic cigarette.

263. The nicotine salt liquid formulation of any one of embodiments 218-262, wherein the formulation is non-toxic to a user of the electronic cigarette.

264. The nicotine salt liquid formulation of any one of embodiments 218-263, further comprising one or more additional nicotine salts in a biologically acceptable liquid carrier suitable for generating the inhalable aerosol upon heating.

265. The nicotine salt liquid formulation of embodiment 264, wherein a second acid used to form the additional nicotine salt is selected from the group consisting of salicylic acid, sorbic acid, benzoic acid, pyruvic acid, lauric acid, and levulinic acid.

266. Use of a nicotine salt formulation for delivery of nicotine to a user from an electronic cigarette wherein the nicotine salt formulation comprises a nicotine salt in a biologically acceptable liquid carrier wherein an acid used to form said nicotine salt is characterized by vapor pressure >20 mmHg at 200° C., and the nicotine salt formulation is heated by the electronic cigarette to generate an aerosol inhalable by the user.

267. Use of a nicotine salt formulation for delivery of nicotine to a user from an electronic cigarette wherein the nicotine salt formulation comprises a nicotine salt in a biologically acceptable liquid carrier wherein an acid used to form said nicotine salt is characterized by vapor pressure of about 20 to 200 mmHg at 200° C., and the nicotine salt formulation is heated by the electronic cigarette to generate an aerosol inhalable by the user.

268. Use of a nicotine salt formulation for delivery of nicotine to a user from an electronic cigarette wherein the nicotine salt formulation comprises a nicotine salt in a biologically acceptable liquid carrier wherein an acid used to form said nicotine salt is further characterized by a melting point <160° C., a boiling point >160° C., and at least a 50-degree difference between the melting point and the boiling point, and the nicotine salt formulation is heated by the electronic cigarette to generate an aerosol inhalable by the user.

269. Use of a nicotine salt formulation for delivery of nicotine to the blood of a user from an electronic cigarette, wherein the nicotine salt formulation in the electronic cigarette is heated to form an aerosol which delivers a level of nicotine in the blood of the user that is at least 5 ng/mL at about 1.5 minutes after a first puff of ten puffs of the aerosol, each puff taken at 30 second intervals.

270. Use of a nicotine salt formulation for delivery of nicotine to a user from an electronic cigarette wherein the nicotine salt formulation comprises a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point, and the nicotine salt formulation is heated by the electronic cigarette to generate an aerosol inhalable by the user.

271. The use of any one of embodiments 266-269, wherein the electronic cigarette heats the nicotine salt formulation to an operating temperature is from 150° C. to 250° C.

272. The use of any one of embodiments 266-269, wherein the electronic cigarette heats the nicotine salt formulation to an operating temperature is from 180° C. to 220° C.

273. The use of any one of embodiments 266-269, wherein the electronic cigarette heats the nicotine salt formulation to an operating temperature is about 200° C.

274. The use of embodiment 270, wherein the operating temperature is from 150° C. to 250° C.

275. The use of embodiment 270, wherein the operating temperature is from 180° C. to 220° C.

276. The use of embodiment 270, wherein the operating temperature is about 200° C.

277. The use of any one of embodiments 266-276, wherein the aerosol comprises condensate of the nicotine salt.

278. The use of any one of embodiments 266-276, wherein the aerosol comprises condensate of freebase nicotine.

279. The use of any one of embodiments 266-276, wherein the aerosol comprises condensate of freebase nicotine and condensate of the carrier.

280. The use of any one of embodiments 266-276, wherein the aerosol comprises condensate of freebase nicotine and condensate of the acid.

281. The use of any one of embodiments 266-280, wherein the aerosol comprises condensate in particle sizes from about 0.1 microns to about 5 microns.

282. The use of any one of embodiments 266-280, wherein the aerosol comprises condensate in particle sizes from about 0.1 microns to about 1 or 2 microns.

283. The use of any one of embodiments 266-280, wherein the aerosol comprises condensate in particle sizes from about 0.1 microns to about 0.7 microns.

284. The use of any one of embodiments 266-280, wherein the aerosol comprises condensate in particle sizes from about 0.3 microns to about 0.4 microns.

285. The use of any one of embodiments 266-284, wherein the acid is a carboxylic acid.

286. The use of any one of embodiments 266-284, wherein the acid used to form said nicotine salt is an organic acid.

287. The use of embodiment 286, wherein the organic acid is monocarboxylic acid, aromatic acid, or keto acid.

288. The use of embodiment 286, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

289. The use of any one of embodiments 266-284, wherein the acid used to form the nicotine salt is salicylic acid.

290. The use of any one of embodiments 266-284, wherein the acid used to form the nicotine salt is benzoic acid.

291. The use of any one of embodiments 266-284, wherein the acid used to form the nicotine salt is pyruvic acid.

292. The use of any one of embodiments 266-284, wherein the acid used to form the nicotine salt is sorbic acid.

293. The use of any one of embodiments 266-284, wherein the acid used to form the nicotine salt is lauric acid.

294. The use of any one of embodiments 266-284, wherein the acid used to form the nicotine salt is levulinic acid.

295. The use of any one of embodiments 266-284, wherein said nicotine salt comprises nicotine pyruvate.

296. The use of any one of embodiments 266-284, wherein said nicotine salt comprises nicotine salicylate.

297. The use of any one of embodiments 266-284, wherein said nicotine salt comprises nicotine sorbate.

298. The use of any one of embodiments 266-284, wherein said nicotine salt comprises nicotine laurate.

299. The use of any one of embodiments 266-284, wherein said nicotine salt comprises nicotine levulinate.

300. The use of any one of embodiments 266-284, wherein said nicotine salt comprises nicotine benzoate.

301. The use of any one of embodiments 266-300, wherein the liquid carrier comprises glycerol, propylene glycol, trimethylene glycol, water, ethanol or combinations thereof.

302. The use of any one of embodiments 266-300, wherein the liquid carrier comprises propylene glycol and vegetable glycerin.

303. The use of any one of embodiments 266-300, wherein the liquid carrier comprises 20% to 50% of propylene glycol and 80% to 50% of vegetable glycerin.

304. The use of any one of embodiments 266-300, wherein the liquid carrier comprises 30% propylene glycol and 70% vegetable glycerin.

305. The use of any one of embodiments 266-304, wherein the nicotine salt is in an amount that forms about 0.5% to about 20% nicotine in the inhalable aerosol.

306. The use of any one of embodiments 266-304, wherein the nicotine salt is in an amount that forms about 1% to about 20% nicotine in the inhalable aerosol.

307. The use of any one of embodiments 266-306, wherein the liquid formulation has a nicotine concentration of about 1% (w/w) to about 25% (w/w).

308. The use of any one of embodiments 266-306, wherein the liquid formulation has a nicotine concentration of about 1% (w/w) to about 20% (w/w).

309. The use of any one of embodiments 266-306, wherein the liquid formulation has a nicotine concentration of about 1% (w/w) to about 18% (w/w).

310. The use of any one of embodiments 266-306, wherein the liquid formulation has a nicotine concentration of about 1% (w/w) to about 15% (w/w).

311. The use of any one of embodiments 266-306, wherein the liquid formulation has a nicotine concentration of about 4% (w/w) to about 12% (w/w).

312. The use of any one of embodiments 266-306, wherein the liquid formulation has a nicotine concentration of about 4% (w/w).

313. The use of any one of embodiments 266-306, wherein the liquid formulation has a nicotine concentration of about 2% (w/w).

314. The use of any one of embodiments 266-313, wherein the formulation further comprises a flavorant.

315. The use of any one of embodiments 266-314, wherein the formulation is non-corrosive to an electronic cigarette.

316. The use of any one of embodiments 266-315, wherein the acid is stable at and below operating temperature or about 200° C.

317. The use of any one of embodiments 266-316, wherein the acid does not decompose at and below operating temperature or about 200° C.

318. The use of any one of embodiments 266-317, wherein the acid does not oxidize at and below operating temperature or about 200° C.

319. The use of any one of embodiments 266-318, wherein the formulation is non-corrosive to the electronic cigarette.

320. The use of any one of embodiments 266-319, wherein the formulation is non-toxic to a user of the electronic cigarette.

321. The use of any one of embodiments 266-320, wherein the formulation further comprises one or more additional nicotine salts in a biologically acceptable liquid carrier suitable for generating the inhalable aerosol upon heating.

322. The use of embodiment 321, wherein a second acid used to form the additional nicotine salt is selected from the group consisting of salicylic acid, sorbic acid, benzoic acid, pyruvic acid, lauric acid, and levulinic acid 323. A cartomizer for an electronic cigarette comprising:
a nicotine salt liquid formulation comprising a nicotine salt in a biologically acceptable liquid carrier wherein an acid used to form said nicotine salt is characterized by vapor pressure >20 mmHg at 200° C.;
an atomizer comprising a heating element in fluid communication with the nicotine salt liquid formulation; and
a fluid storage compartment that stores the nicotine salt liquid formulation.

324. A cartomizer for an electronic cigarette comprising:
a nicotine salt liquid formulation comprising a nicotine salt in a biologically acceptable liquid carrier wherein an acid used to form said nicotine salt is characterized by vapor pressure of about 20 to 200 mmHg at 200° C.;
an atomizer comprising a heating element in fluid communication with the nicotine salt liquid formulation; and
a fluid storage compartment that stores the nicotine salt liquid formulation.

325. A cartomizer for an electronic cigarette comprising:
a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
an atomizer comprising a heating element in fluid communication with the nicotine salt liquid formulation; and
a fluid storage compartment that stores the nicotine salt liquid formulation.

326. A cartomizer for an electronic cigarette comprising:
a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
an atomizer comprising a heating element in fluid communication with the nicotine salt liquid formulation; and
a fluid storage compartment that stores the nicotine salt liquid formulation.

327. The cartomizer of any one of embodiments 323-325, wherein the electronic cigarette heats the nicotine salt formulation to an operating temperature from 150° C. to 250° C.

328. The cartomizer of any one of embodiments 323-325, wherein the electronic cigarette heats the nicotine salt formulation to an operating temperature from 180° C. to 220° C.

329. The cartomizer of any one of embodiments 323-325, wherein the electronic cigarette heats the nicotine salt formulation to an operating temperature of about 200° C.

330. The cartomizer of embodiment 326, wherein the operating temperature is from 150° C. to 250° C.

331. The cartomizer of embodiment 326, wherein the operating temperature is from 180° C. to 220° C.

332. The cartomizer of embodiment 326, wherein the operating temperature is about 200° C.

333. The cartomizer of any one of embodiments 323-332, wherein the cartomizer further comprises a mouthpiece.

334. The cartomizer of any one of embodiments 323-333, wherein the acid is a carboxylic acid.

335. The cartomizer of any one of embodiments 323-333, wherein the acid used to form said nicotine salt is an organic acid.

336. The cartomizer of embodiment 335, wherein the organic acid is monocarboxylic acid, aromatic acid, or keto acid.

337. The cartomizer of embodiment 335, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

338. The cartomizer of any one of embodiments 323-333, wherein the acid used to form the nicotine salt is salicylic acid.

339. The cartomizer of any one of embodiments 323-333, wherein the acid used to form the nicotine salt is benzoic acid.

340. The cartomizer of any one of embodiments 323-333, wherein the acid used to form the nicotine salt is pyruvic acid.

341. The cartomizer of any one of embodiments 323-333, wherein the acid used to form the nicotine salt is sorbic acid.

342. The cartomizer of any one of embodiments 323-333, wherein the acid used to form the nicotine salt is lauric acid.

343. The cartomizer of any one of embodiments 323-333, wherein the acid used to form the nicotine salt is levulinic acid.

344. The cartomizer of any one of embodiments 323-333, wherein said nicotine salt comprises nicotine pyruvate.

345. The cartomizer of any one of embodiments 323-333, wherein said nicotine salt comprises nicotine salicylate.

346. The cartomizer of any one of embodiments 323-333, wherein said nicotine salt comprises nicotine sorbate.

347. The cartomizer of any one of embodiments 323-333, wherein said nicotine salt comprises nicotine laurate.

348. The cartomizer of any one of embodiments 323-333, wherein said nicotine salt comprises nicotine levulinate.

349. The cartomizer of any one of embodiments 323-333, wherein said nicotine salt comprises nicotine benzoate.

350. The cartomizer of any one of embodiments 323-349, wherein the liquid carrier comprises glycerol, propylene glycol, trimethylene glycol, water, ethanol or combinations thereof.

351. The cartomizer of any one of embodiments 323-349, wherein the liquid carrier comprises propylene glycol and vegetable glycerin.

352. The cartomizer of any one of embodiments 323-349, wherein the liquid carrier comprises 20% to 50% of propylene glycol and 80% to 50% of vegetable glycerin.

353. The cartomizer of any one of embodiments 323-349, wherein the liquid carrier comprises 30% propylene glycol and 70% vegetable glycerin.

354. The cartomizer of any one of embodiments 323-353, wherein the liquid formulation has a nicotine concentration of about 1% (w/w) to about 25% (w/w).

355. The cartomizer of any one of embodiments 323-353, wherein the liquid formulation has a nicotine concentration of about 1% (w/w) to about 20% (w/w).

356. The cartomizer of any one of embodiments 323-353, wherein the liquid formulation has a nicotine concentration of about 1% (w/w) to about 18% (w/w).

357. The cartomizer of any one of embodiments 323-353, wherein the liquid formulation has a nicotine concentration of about 1% (w/w) to about 15% (w/w).

358. The cartomizer of any one of embodiments 323-353, wherein the liquid formulation has a nicotine concentration of about 4% (w/w) to about 12% (w/w).

359. The cartomizer of any one of embodiments 323-353, wherein the liquid formulation has a nicotine concentration of about 4% (w/w).

360. The cartomizer of any one of embodiments 323-353, wherein the liquid formulation has a nicotine concentration of about 2% (w/w).

361. The cartomizer of any one of embodiments 323-360, wherein the electronic cigarette is configured to generate an aerosol inhalable by a user.

362. The cartomizer of embodiment 361, wherein the aerosol comprises condensate of the nicotine salt.

363. The cartomizer of embodiment 361, wherein the aerosol comprises condensate of freebase nicotine.

364. The cartomizer of embodiment 361, wherein the aerosol comprises condensate of freebase nicotine and condensate of the carrier.

365. The cartomizer of embodiment 361, wherein the aerosol comprises condensate of freebase nicotine and condensate of the acid.

366. The cartomizer of any one of embodiments 361-365, wherein the aerosol comprises condensate in particle sizes from about 0.1 microns to about 5 microns.

367. The cartomizer of any one of embodiments 361-365, wherein the aerosol comprises condensate in particle sizes from about 0.1 microns to about 1 or 2 microns.

368. The cartomizer of any one of embodiments 361-365, wherein the aerosol comprises condensate in particle sizes from about 0.1 microns to about 0.7 microns.

369. The cartomizer of any one of embodiments 361-365, wherein the aerosol comprises condensate in particle sizes from about 0.3 microns to about 0.4 microns.

370. The cartomizer of any one of embodiments 361-369, wherein the nicotine salt is in an amount that forms about 0.5% to about 20% nicotine in the inhalable aerosol.

371. The cartomizer of any one of embodiments 361-369, wherein the nicotine salt is in an amount that forms about 1% to about 20% nicotine in the inhalable aerosol.

372. The cartomizer of any one of embodiments 323-371, wherein the formulation further comprises a flavorant.

373. The cartomizer of any one of embodiments 323-372, wherein the formulation is non-corrosive to an electronic cigarette.

374. The cartomizer of any one of embodiments 323-373, wherein the acid is stable at and below operating temperature or about 200° C.

375. The cartomizer of any one of embodiments 323-374, wherein the acid does not decompose at and below operating temperature or about 200° C.

376. The cartomizer of any one of embodiments 323-375, wherein the acid does not oxidize at and below operating temperature or about 200° C.

377. The cartomizer of any one of embodiments 323-376, wherein the formulation is non-corrosive to the electronic cigarette.

378. The cartomizer of any one of embodiments 323-377, wherein the formulation is non-toxic to a user of the electronic cigarette.

379. The cartomizer of any one of embodiments 323-378, wherein the formulation further comprises one or more additional nicotine salts in a biologically acceptable liquid carrier suitable for generating the inhalable aerosol upon heating.

380. The cartomizer of embodiment 379, wherein a second acid used to form the additional nicotine salt is selected from the group consisting of salicylic acid, sorbic acid, benzoic acid, pyruvic acid, lauric acid, and levulinic acid.

381. An electronic cigarette for generating an inhalable aerosol comprising
    a fluid storage compartment;
    a heater; and
    a nicotine salt liquid formulation in the fluid storage compartment, the liquid formulation comprising a nicotine salt in a biologically acceptable liquid carrier wherein an acid used to form said nicotine salt is characterized by vapor pressure >20 mmHg at 200° C.;
    a battery; and
    a mouthpiece.

382. An electronic cigarette for generating an inhalable aerosol comprising
  a fluid storage compartment;
  a heater; and
  a nicotine salt liquid formulation in the fluid storage compartment, the liquid formulation comprising a nicotine salt in a biologically acceptable liquid carrier wherein an acid used to form said nicotine salt is characterized by vapor pressure of about 20 to 200 mmHg at 200° C.;
  a battery; and
  a mouthpiece.

383. An electronic cigarette for generating an inhalable aerosol comprising
  a fluid storage compartment;
  a heater; and
  a nicotine salt liquid formulation in the fluid storage compartment, the liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
  a battery; and
  a mouthpiece.

384. An electronic cigarette for generating an inhalable aerosol comprising
  a fluid storage compartment;
  a heater; and
  a nicotine salt liquid formulation in the fluid storage compartment, the liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
  a battery; and
  a mouthpiece.

385. The electronic cigarette of any one of embodiments 381-384, wherein the heater comprises a heater chamber, a fluid wick, and a resistive heating element in contact with the fluid wick.

386. The electronic cigarette of any one of embodiments 381-384, wherein the mouthpiece, the heater and the fluid storage compartment form a cartomizer separable from the battery.

387. The electronic cigarette of any one of embodiments 381-384, wherein the heater and the fluid storage compartment form a cartomizer separable from the battery and the mouthpiece.

388. The electronic cigarette of any one of embodiments 381-384, wherein the fluid storage compartment is separable from the heater, the battery and the mouthpiece.

389. The electronic cigarette of any one of embodiments 381-383, wherein the electronic cigarette heats the nicotine salt formulation to an operating temperature from 150° C. to 250° C.

390. The electronic cigarette of any one of embodiments 381-383, wherein the electronic cigarette heats the nicotine salt formulation to an operating temperature from 180° C. to 220° C.

391. The electronic cigarette of any one of embodiments 381-383, wherein the electronic cigarette heats the nicotine salt formulation to an operating temperature of about 200° C.

392. The electronic cigarette of embodiment 384, wherein the operating temperature is from 150° C. to 250° C.

393. The electronic cigarette of embodiment 384, wherein the operating temperature is from 180° C. to 220° C.

394. The electronic cigarette of embodiment 384, wherein the operating temperature is about 200° C.

395. The electronic cigarette of any one of embodiments 381-394, wherein the aerosol comprises condensate of the nicotine salt.

396. The electronic cigarette of any one of embodiments 381-394, wherein the aerosol comprises condensate of freebase nicotine.

397. The electronic cigarette of any one of embodiments 381-394, wherein the aerosol comprises condensate of freebase nicotine and condensate of the carrier.

398. The electronic cigarette of any one of embodiments 381-394, wherein the aerosol comprises condensate of freebase nicotine and condensate of the acid.

399. The electronic cigarette of any one of embodiments 381-398, wherein the aerosol comprises condensate in particle sizes from about 0.1 microns to about 5 microns.

400. The electronic cigarette of any one of embodiments 381-398, wherein the aerosol comprises condensate in particle sizes from about 0.1 microns to about 1 or 2 microns.

401. The electronic cigarette of any one of embodiments 381-398, wherein the aerosol comprises condensate in particle sizes from about 0.1 microns to about 0.7 microns.

402. The electronic cigarette of any one of embodiments 381-398, wherein the aerosol comprises condensate in particle sizes from about 0.3 microns to about 0.4 microns.

403. The electronic cigarette of any one of embodiments 381-402, wherein the acid is a carboxylic acid.

404. The electronic cigarette of any one of embodiments 381-402, wherein the acid used to form said nicotine salt is an organic acid.

405. The electronic cigarette of embodiment 404, wherein the organic acid is monocarboxylic acid, aromatic acid, or keto acid.

406. The electronic cigarette of embodiment 404, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

407. The electronic cigarette of any one of embodiments 381-402, wherein the acid used to form the nicotine salt is salicylic acid.

408. The electronic cigarette of any one of embodiments 381-402, wherein the acid used to form the nicotine salt is benzoic acid.

409. The electronic cigarette of any one of embodiments 381-402, wherein the acid used to form the nicotine salt is pyruvic acid.

410. The electronic cigarette of any one of embodiments 381-402, wherein the acid used to form the nicotine salt is sorbic acid.

411. The electronic cigarette of any one of embodiments 381-402, wherein the acid used to form the nicotine salt is lauric acid.

412. The electronic cigarette of any one of embodiments 381-402, wherein the acid used to form the nicotine salt is levulinic acid.

413. The electronic cigarette of any one of embodiments 381-402, wherein said nicotine salt comprises nicotine pyruvate.

414. The electronic cigarette of any one of embodiments 381-402, wherein said nicotine salt comprises nicotine salicylate.

415. The electronic cigarette of any one of embodiments 381-402, wherein said nicotine salt comprises nicotine sorbate.

416. The electronic cigarette of any one of embodiments 381-402, wherein said nicotine salt comprises nicotine laurate.

417. The electronic cigarette of any one of embodiments 381-402, wherein said nicotine salt comprises nicotine levulinate.

418. The electronic cigarette of any one of embodiments 381-402, wherein said nicotine salt comprises nicotine benzoate.

419. The electronic cigarette of any one of embodiments 381-419, wherein the liquid carrier comprises glycerol, propylene glycol, trimethylene glycol, water, ethanol or combinations thereof.

420. The electronic cigarette of any one of embodiments 381-419, wherein the liquid carrier comprises propylene glycol and vegetable glycerin.

421. The electronic cigarette of any one of embodiments 381-419, wherein the liquid carrier comprises 20% to 50% of propylene glycol and 80% to 50% of vegetable glycerin.

422. The electronic cigarette of any one of embodiments 381-419, wherein the liquid carrier comprises 30% propylene glycol and 70% vegetable glycerin.

423. The electronic cigarette of any one of embodiments 381-422, wherein the nicotine salt is in an amount that forms about 0.5% to about 20% nicotine in the inhalable aerosol.

424. The electronic cigarette of any one of embodiments 381-422, wherein the nicotine salt is in an amount that forms about 1% to about 20% nicotine in the inhalable aerosol.

425. The electronic cigarette of any one of embodiments 381-424, wherein the liquid formulation has a nicotine concentration of about 1% (w/w) to about 25% (w/w).

426. The electronic cigarette of any one of embodiments 381-424, wherein the liquid formulation has a nicotine concentration of about 1% (w/w) to about 20% (w/w).

427. The electronic cigarette of any one of embodiments 381-424, wherein the liquid formulation has a nicotine concentration of about 1% (w/w) to about 18% (w/w).

428. The electronic cigarette of any one of embodiments 381-424, wherein the liquid formulation has a nicotine concentration of about 1% (w/w) to about 15% (w/w).

429. The electronic cigarette of any one of embodiments 381-424, wherein the liquid formulation has a nicotine concentration of about 4% (w/w) to about 12% (w/w).

430. The electronic cigarette of any one of embodiments 381-424, wherein the liquid formulation has a nicotine concentration of about 4% (w/w).

431. The electronic cigarette of any one of embodiments 381-424, wherein the liquid formulation has a nicotine concentration of about 2% (w/w).

432. The electronic cigarette of any one of embodiments 381-431, wherein the formulation further comprises a flavorant.

433. The electronic cigarette of any one of embodiments 381-432, wherein the formulation is non-corrosive to an electronic cigarette.

434. The electronic cigarette of any one of embodiments 381-433, wherein the acid is stable at and below operating temperature or about 200° C.

435. The electronic cigarette of any one of embodiments 381-434, wherein the acid does not decompose at and below operating temperature or about 200° C.

436. The electronic cigarette of any one of embodiments 381-435, wherein the acid does not oxidize at and below operating temperature or about 200° C.

437. The electronic cigarette of any one of embodiments 381-436, wherein the formulation is non-corrosive to the electronic cigarette.

438. The electronic cigarette of any one of embodiments 381-437, wherein the formulation is non-toxic to a user of the electronic cigarette.

439. The electronic cigarette of any one of embodiments 381-438, wherein the formulation further comprises one or more additional nicotine salts in a biologically acceptable liquid carrier suitable for generating the inhalable aerosol upon heating.

440. The electronic cigarette of embodiment 439, wherein a second acid used to form the additional nicotine salt is selected from the group consisting of salicylic acid, sorbic acid, benzoic acid, pyruvic acid, lauric acid, and levulinic acid.

441. A cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure >20 mmHg at 200° C.

442. A cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure of about 20 to 200 mmHg at 200° C.

443. A cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

444. A cartridge in an electronic cigarette comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

445. The cartridge of any one of embodiments 441-444, wherein the cartridge is separable from the electronic cigarette.

446. The cartridge of any one of embodiments 441-445, wherein the acid is a carboxylic acid.

447. The cartridge of any one of embodiments 441-445, wherein the acid used to form said nicotine salt is an organic acid.

448. The cartridge of embodiment 447, wherein the organic acid is monocarboxylic acid, aromatic acid, or keto acid.

449. The cartridge of embodiment 447, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

450. The cartridge of any one of embodiments 441-445, wherein the acid used to form the nicotine salt is salicylic acid.

451. The cartridge of any one of embodiments 441-445, wherein the acid used to form the nicotine salt is benzoic acid.

452. The cartridge of any one of embodiments 441-445, wherein the acid used to form the nicotine salt is pyruvic acid.

453. The cartridge of any one of embodiments 441-445, wherein the acid used to form the nicotine salt is sorbic acid.

454. The cartridge of any one of embodiments 441-445, wherein the acid used to form the nicotine salt is lauric acid.

455. The cartridge of any one of embodiments 441-445, wherein the acid used to form the nicotine salt is levulinic acid.

456. The cartridge of any one of embodiments 441-445, wherein said nicotine salt comprises nicotine pyruvate.

457. The cartridge of any one of embodiments 441-445, wherein said nicotine salt comprises nicotine salicylate.

458. The cartridge of any one of embodiments 441-445, wherein said nicotine salt comprises nicotine sorbate.

459. The cartridge of any one of embodiments 441-445, wherein said nicotine salt comprises nicotine laurate.

460. The cartridge of any one of embodiments 441-445, wherein said nicotine salt comprises nicotine levulinate.

461. The cartridge of any one of embodiments 441-445, wherein said nicotine salt comprises nicotine benzoate.

462. The cartridge of any one of embodiments 441-461, wherein the liquid carrier comprises glycerol, propylene glycol, trimethylene glycol, water, ethanol or combinations thereof.

463. The cartridge of any one of embodiments 441-461, wherein the liquid carrier comprises propylene glycol and vegetable glycerin.

464. The cartridge of any one of embodiments 441-461, wherein the liquid carrier comprises 20% to 50% of propylene glycol and 80% to 50% of vegetable glycerin.

465. The cartridge of any one of embodiments 441-461, wherein the liquid carrier comprises 30% propylene glycol and 70% vegetable glycerin.

466. The cartridge of any one of embodiments 441-465, wherein the liquid formulation has a nicotine concentration of about 1% (w/w) to about 25% (w/w).

467. The cartridge of any one of embodiments 441-465, wherein the liquid formulation has a nicotine concentration of about 1% (w/w) to about 20% (w/w).

468. The cartridge of any one of embodiments 441-465, wherein the liquid formulation has a nicotine concentration of about 1% (w/w) to about 18% (w/w).

469. The cartridge of any one of embodiments 441-465, wherein the liquid formulation has a nicotine concentration of about 1% (w/w) to about 15% (w/w).

470. The cartridge of any one of embodiments 441-465, wherein the liquid formulation has a nicotine concentration of about 4% (w/w) to about 12% (w/w).

471. The cartridge of any one of embodiments 441-465, wherein the liquid formulation has a nicotine concentration of about 4% (w/w).

472. The cartridge of any one of embodiments 441-465, wherein the liquid formulation has a nicotine concentration of about 2% (w/w).

473. The cartridge of any one of embodiments 441-472, wherein the formulation further comprises a flavorant.

474. The cartridge of any one of embodiments 441-473, wherein the formulation is non-corrosive to an electronic cigarette.

475. The cartridge of any one of embodiments 441-474, wherein the acid is stable at and below operating temperature or about 200° C.

476. The cartridge of any one of embodiments 441-475, wherein the acid does not decompose at and below operating temperature or about 200° C.

477. The cartridge of any one of embodiments 441-476, wherein the acid does not oxidize at and below operating temperature or about 200° C.

478. The cartridge of any one of embodiments 441-477, wherein the formulation is non-corrosive to the electronic cigarette.

479. The cartridge of any one of embodiments 441-478, wherein the formulation is non-toxic to a user of the electronic cigarette.

480. The cartridge of any one of embodiments 441-479, wherein the formulation further comprises one or more additional nicotine salts in a biologically acceptable liquid carrier suitable for generating the inhalable aerosol upon heating.

481. The cartridge of embodiment 480, wherein a second acid used to form the additional nicotine salt is selected from the group consisting of salicylic acid, sorbic acid, benzoic acid, pyruvic acid, lauric acid, and levulinic acid.

482. A kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure >20 mmHg at 200° C.;
  iii. a heater;
  iv. a battery; and
  v. a mouthpiece; and
(b) instructions for using the electronic cigarette to generate an inhalable aerosol.

483. A kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure of about 20 to 200 mmHg at 200° C.;
  iii. a heater;
  iv. a battery; and
  v. a mouthpiece; and
(b) instructions for using the electronic cigarette to generate an inhalable aerosol.

484. A kit comprising:
(a) an electronic cigarette for generating an inhalable aerosol comprising
  i. a device body comprising a cartridge receptacle;
  ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point;
iii. a heater;
iv. a battery; and
v. a mouthpiece; and
(b) instructions for using the electronic cigarette to generate an inhalable aerosol.

485. A kit comprising:
(a) an electronic cigarette for generating an inhalable aerosol comprising
i. a device body comprising a cartridge receptacle;
ii. a cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point;
iii. a heater;
iv. a battery; and
v. a mouthpiece; and
(b) instructions for using the electronic cigarette to generate an inhalable aerosol.

486. The kit of any one of embodiments 482-485, wherein the acid is a carboxylic acid.

487. The kit of any one of embodiments 482-485, wherein the acid used to form said nicotine salt is an organic acid.

488. The kit of embodiment 487, wherein the organic acid is monocarboxylic acid, aromatic acid, or keto acid.

489. The kit of embodiment 487, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

490. The kit of any one of embodiments 482-485, wherein the acid used to form the nicotine salt is salicylic acid.

491. The kit of any one of embodiments 482-485, wherein the acid used to form the nicotine salt is benzoic acid.

492. The kit of any one of embodiments 482-485, wherein the acid used to form the nicotine salt is pyruvic acid.

493. The kit of any one of embodiments 482-485, wherein the acid used to form the nicotine salt is sorbic acid.

494. The kit of any one of embodiments 482-485, wherein the acid used to form the nicotine salt is lauric acid.

495. The kit of any one of embodiments 482-485, wherein the acid used to form the nicotine salt is levulinic acid.

496. The kit of any one of embodiments 482-485, wherein said nicotine salt comprises nicotine pyruvate.

497. The kit of any one of embodiments 482-485, wherein said nicotine salt comprises nicotine salicylate.

498. The kit of any one of embodiments 482-485, wherein said nicotine salt comprises nicotine sorbate.

499. The kit of any one of embodiments 482-485, wherein said nicotine salt comprises nicotine laurate.

500. The kit of any one of embodiments 482-485, wherein said nicotine salt comprises nicotine levulinate.

501. The kit of any one of embodiments 482-485, wherein said nicotine salt comprises nicotine benzoate.

502. The kit of any one of embodiments 482-501, wherein the liquid carrier comprises glycerol, propylene glycol, trimethylene glycol, water, ethanol or combinations thereof.

503. The kit of any one of embodiments 482-501, wherein the liquid carrier comprises propylene glycol and vegetable glycerin.

504. The kit of any one of embodiments 482-501, wherein the liquid carrier comprises 20% to 50% of propylene glycol and 80% to 50% of vegetable glycerin.

505. The kit of any one of embodiments 482-501, wherein the liquid carrier comprises 30% propylene glycol and 70% vegetable glycerin.

506. The kit of any one of embodiments 482-505, wherein the liquid formulation has a nicotine concentration of about 1% (w/w) to about 25% (w/w).

507. The kit of any one of embodiments 482-505, wherein the liquid formulation has a nicotine concentration of about 1% (w/w) to about 20% (w/w).

508. The kit of any one of embodiments 482-505, wherein the liquid formulation has a nicotine concentration of about 1% (w/w) to about 18% (w/w).

509. The kit of any one of embodiments 482-505, wherein the liquid formulation has a nicotine concentration of about 1% (w/w) to about 15% (w/w).

510. The kit of any one of embodiments 482-505, wherein the liquid formulation has a nicotine concentration of about 4% (w/w) to about 12% (w/w).

511. The kit of any one of embodiments 482-505, wherein the liquid formulation has a nicotine concentration of about 4% (w/w).

512. The kit of any one of embodiments 482-505, wherein the liquid formulation has a nicotine concentration of about 2% (w/w).

513. The kit of any one of embodiments 482-512, wherein the formulation further comprises a flavorant.

514. The kit of any one of embodiments 482-513, wherein the formulation is non-corrosive to an electronic cigarette.

515. The kit of any one of embodiments 482-514, wherein the acid is stable at and below operating temperature or about 200° C.

516. The kit of any one of embodiments 482-515, wherein the acid does not decompose at and below operating temperature or about 200° C.

517. The kit of any one of embodiments 482-516, wherein the acid does not oxidize at and below operating temperature or about 200° C.

518. The kit of any one of embodiments 482-517, wherein the formulation is non-corrosive to the electronic cigarette.

519. The kit of any one of embodiments 482-518, wherein the formulation is non-toxic to a user of the electronic cigarette.

520. The kit of any one of embodiments 482-519, wherein the formulation further comprises one or more additional nicotine salts in a biologically acceptable liquid carrier suitable for generating the inhalable aerosol upon heating.

521. The kit of embodiment 520, wherein a second acid used to form the additional nicotine salt is selected from the group consisting of salicylic acid, sorbic acid, benzoic acid, pyruvic acid, lauric acid, and levulinic acid.

522. A cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure >20 mmHg at 200° C.

523. A cartridge comprising a fluid storage compartment, wherein the fluid storage compartment stores a nicotine salt liquid formulation comprising a nicotine salt in a biologically acceptable liquid carrier wherein an acid used to form said nicotine salt is characterized by vapor pressure of about 20 to 200 mmHg at 200° C.

524. A cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point <160° C., a boiling point >160° C., and at least a 50-degree difference between the melting point and the boiling point.

525. A cartridge comprising a fluid storage compartment, wherein the fluid storage compartment stores a nicotine salt liquid formulation comprising a nicotine salt in a biologically acceptable liquid carrier wherein an acid used to form said nicotine salt is further characterized by a melting point at least 40 degrees lower than an operating temperature of the electronic cigarette, a boiling point no more than 40 degrees lower than the operating temperature of the electronic cigarette, and at least a 50-degree difference between the melting point and the boiling point.

526. The cartridge of any one of embodiments 523-526, wherein the cartridge can be connected to an electronic cigarette.

527. The cartridge of any one of embodiments 523-527, wherein the acid is a carboxylic acid.

528. The cartridge of any one of embodiments 523-527, wherein the acid used to form said nicotine salt is an organic acid.

529. The cartridge of embodiment 529, wherein the organic acid is monocarboxylic acid, aromatic acid, or keto acid.

530. The cartridge of embodiment 529, wherein the organic acid is formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, finnaric acid, gluconic acid, saccharic acid, salicylic acid, sorbic acid, malonic acid, or malic acid.

531. The cartridge of any one of embodiments 523-527, wherein the acid used to form the nicotine salt is salicylic acid.

532. The cartridge of any one of embodiments 523-527, wherein the acid used to form the nicotine salt is benzoic acid.

533. The cartridge of any one of embodiments 523-527, wherein the acid used to form the nicotine salt is pyruvic acid.

534. The cartridge of any one of embodiments 523-527, wherein the acid used to form the nicotine salt is sorbic acid.

535. The cartridge of any one of embodiments 523-527, wherein the acid used to form the nicotine salt is lauric acid.

536. The cartridge of any one of embodiments 523-527, wherein the acid used to form the nicotine salt is levulinic acid.

537. The cartridge of any one of embodiments 523-527, wherein said nicotine salt comprises nicotine pyruvate.

538. The cartridge of any one of embodiments 523-527, wherein said nicotine salt comprises nicotine salicylate.

539. The cartridge of any one of embodiments 523-527, wherein said nicotine salt comprises nicotine sorbate.

540. The cartridge of any one of embodiments 523-527, wherein said nicotine salt comprises nicotine laurate.

541. The cartridge of any one of embodiments 523-527, wherein said nicotine salt comprises nicotine levulinate.

542. The cartridge of any one of embodiments 523-527, wherein said nicotine salt comprises nicotine benzoate.

543. The cartridge of any one of embodiments 523-543, wherein the liquid carrier comprises glycerol, propylene glycol, trimethylene glycol, water, ethanol or combinations thereof.

544. The cartridge of any one of embodiments 523-543, wherein the liquid carrier comprises propylene glycol and vegetable glycerin.

545. The cartridge of any one of embodiments 523-543, wherein the liquid carrier comprises 20% to 50% of propylene glycol and 80% to 50% of vegetable glycerin.

546. The cartridge of any one of embodiments 523-543, wherein the liquid carrier comprises 30% propylene glycol and 70% vegetable glycerin.

547. The cartridge of any one of embodiments 523-547, wherein the liquid formulation has a nicotine concentration of about 1% (w/w) to about 25% (w/w).

548. The cartridge of any one of embodiments 523-547, wherein the liquid formulation has a nicotine concentration of about 1% (w/w) to about 20% (w/w).

549. The cartridge of any one of embodiments 523-547, wherein the liquid formulation has a nicotine concentration of about 1% (w/w) to about 18% (w/w).

550. The cartridge of any one of embodiments 523-547, wherein the liquid formulation has a nicotine concentration of about 1% (w/w) to about 15% (w/w).

551. The cartridge of any one of embodiments 523-547, wherein the liquid formulation has a nicotine concentration of about 4% (w/w) to about 12% (w/w).

552. The cartridge of any one of embodiments 523-547, wherein the liquid formulation has a nicotine concentration of about 4% (w/w).

553. The cartridge of any one of embodiments 523-547, wherein the liquid formulation has a nicotine concentration of about 2% (w/w).

554. The cartridge of any one of embodiments 523-553, wherein the formulation further comprises a flavorant.

555. The cartridge of any one of embodiments 523-554, wherein the formulation is non-corrosive to an electronic cigarette.

556. The cartridge of any one of embodiments 523-555, wherein the acid is stable at and below operating temperature or about 200° C.

557. The cartridge of any one of embodiments 523-556, wherein the acid does not decompose at and below operating temperature or about 200° C.

558. The cartridge of any one of embodiments 523-557, wherein the acid does not oxidize at and below operating temperature or about 200° C.

559. The cartridge of any one of embodiments 523-558, wherein the formulation is non-corrosive to the electronic cigarette.

560. The cartridge of any one of embodiments 523-559, wherein the formulation is non-toxic to a user of the electronic cigarette.

561. The cartridge of any one of embodiments 523-560, wherein the formulation further comprises one or more additional nicotine salts in a biologically acceptable liquid carrier suitable for generating the inhalable aerosol upon heating.

562. The cartridge of embodiment 561, wherein a second acid used to form the additional nicotine salt is selected from the group consisting of salicylic acid, sorbic acid, benzoic acid, pyruvic acid, lauric acid, and levulinic acid.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following embodiments define the scope of the invention and that methods and structures within the scope of these embodiments and their equivalents be covered thereby.

What is claimed is:

1. A method of delivering nicotine to a user comprising deploying an electronic cigarette comprising a nicotine formulation that comprises nicotine, an acid, wherein the acid comprises pyruvic acid, salicylic acid, sorbic acid, lauric acid, levulinic acid, or benzoic acid, and a biologically acceptable liquid carrier, wherein:
   a. the nicotine formulation has a pH between 2.1-6.7;
   b. the nicotine concentration is from about 2% (w/w) to about 6% (w/w);
   c. operation of the electronic cigarette comprises heating at least a portion of the nicotine formulation to generate an inhalable aerosol comprising particle sizes from about 0.1 microns to about 5 microns; and
   d. inhalation of the inhalable aerosol into the user's lungs over a period of about 5 minutes at a rate of about one inhalation per 30 seconds results in a nicotine plasma Tmax from about 3 min to about 8 min.

2. The method of claim 1, wherein the nicotine plasma Tmax is from about 3 min to about 7 min, from about 3 min to about 6 min, from about 3 min to about 5 min, from about 3 min to about 4 min, from about 4 min to about 8 min, from about 4 min to about 7 min, from about 4 min to about 6 min, from about 4 min to about 5 min, from about 5 min to about 8 min, from about 5 min to about 7 min, from about 5 min to about 6 min, from about 6 min to about 8 min, from about 6 min to about 7 min, from about 7 min to about 8 min, less than about 8 min, less than about 7 min, less than about 6 min, less than about 5 min, less than about 4 min, about 8 min, about 7 min, about 6 min, about 5 min, about 4 min, or about 3 min.

3. The method of claim 1, wherein the Tmax is determined based on at least three independent data sets.

4. The method of claim 1, wherein the Tmax is a range of at least three independent data sets.

5. The method of claim 1, wherein the Tmax is an average±a standard deviation of at least three independent data sets.

6. The method of claim 1, wherein the nicotine formulation comprises a nicotine salt comprising nicotine and an acid.

7. The method of claim 6, wherein nicotine formulation comprises monoprotonated nicotine.

8. The method of claim 1, wherein the acid does not decompose at room temperature and does not decompose at the operating temperature of the electronic cigarette.

9. The method of claim 1, wherein the acid comprises one carboxylic acid functional group.

10. The method of claim 1, wherein the acid comprises benzoic acid.

11. The method of claim 1, wherein the nicotine concentration is about 5% (w/w).

12. A method of delivering nicotine to a user comprising deploying an electronic cigarette comprising a nicotine formulation that comprises nicotine, an acid, wherein the acid comprises pyruvic acid, salicylic acid, sorbic acid, lauric acid, levulinic acid, or benzoic acid and a biologically acceptable liquid carrier, wherein:
   a. the nicotine formulation has a pH between 2.1-6.7
   b. operation of the electronic cigarette comprises heating at least a portion of the nicotine formulation to generate an inhalable aerosol comprising particle sizes from about 0.1 microns to about 5 microns;
   c. inhalation of the inhalable aerosol into the user's lungs over a period of about 5 minutes at a rate of about one inhalation per 30 seconds results in a nicotine plasma Tmax from about 3 min to about 8 min;
   d. the nicotine concentration is from about 2% (w/w) to about 6% (w/w);
   e. the nicotine formulation comprises monoprotonated nicotine; and
   f. the acid does not decompose at room temperature and does not decompose at the operating temperature of the electronic cigarette.

13. The method of claim 12, wherein the acid comprises benzoic acid.

14. The method of claim 13, wherein the nicotine concentration is about 5% (w/w).

15. A method of delivering nicotine to a user comprising deploying an electronic cigarette comprising a nicotine formulation comprising nicotine and benzoic acid in a biologically acceptable liquid carrier, wherein:
   a. the nicotine formulation has a pH between 2.1-6.7;
   b. the nicotine concentration is from about 2% (w/w) to about 6% (w/w);
   c. operation of the electronic cigarette comprises heating at least a portion of the nicotine formulation to generate an inhalable aerosol comprising particle sizes from about 0.1 microns to about 5 microns; and
   d. inhalation of the inhalable aerosol into the user's lungs over a period of about 5 minutes at a rate of about one inhalation per 30 seconds results in a nicotine plasma Tmax from about 5 min to about 8 min.

16. A cartridge for use with an electronic cigarette comprising a fluid compartment configured to be in fluid communication with a heating element, the fluid compartment comprising a nicotine formulation that comprises nicotine and an acid, wherein the acid comprises pyruvic acid, salicylic acid, sorbic acid, lauric acid, levulinic acid, or benzoic acid, and a biologically acceptable liquid carrier, wherein:
   a. the nicotine formulation has a pH between 2.1-6.7
   b. the nicotine concentration is from about 2% (w/w) to about 6% (w/w);
   c. operation of the electronic cigarette comprises heating at least a portion of the nicotine formulation to generate an inhalable aerosol comprising particle sizes from about 0.1 microns to about 5 microns; and wherein
   d. inhalation of the inhalable aerosol into the user's lungs over a period of about 5 minutes at a rate of about one inhalation per 30 seconds results in a nicotine plasma Tmax from about 3 min to about 8 min.

17. The cartridge of claim 16, wherein the nicotine plasma Tmax is from about 3 min to about 7 min, from about 3 min to about 6 min, from about 3 min to about 5 min, from about 3 min to about 4 min, from about 4 min to about 8 min, from about 4 min to about 7 min, from about 4 min to about 6 min, from about 4 min to about 5 min, from about 5 min to about 8 min, from about 5 min to about 7 min, from about 5 min to about 6 min, from about 6 min to about 8 min, from about 6 min to about 7 min, from about 7 min to about 8 min, less than about 8 min, less than about 7 min, less than about 6 min, less than about 5 min, less than about 4 min, about 8 min, about 7 min, about 6 min, about 5 min, about 4 min, or about 3 min.

18. The cartridge of claim 16, wherein the Tmax is determined based on at least three independent data sets.

19. The cartridge of claim 16, wherein the Tmax is a range of at least three independent data sets.

20. The cartridge of claim 16, wherein the Tmax is an average±a standard deviation of at least three independent data sets.

21. The cartridge of claim 16, wherein the nicotine formulation comprises a nicotine salt comprising nicotine and an acid.

22. The cartridge of claim 21, wherein nicotine formulation comprises monoprotonated nicotine.

23. The cartridge of claim 21, wherein the acid does not decompose at room temperature and does not decompose at the operating temperature of the electronic cigarette.

24. The cartridge of claim 21, wherein the acid comprises one carboxylic acid functional group.

25. The cartridge of claim 16, wherein the acid comprises benzoic acid.

26. The cartridge of claim 16, wherein the nicotine concentration is about 5% (w/w).

\* \* \* \* \*